(12) United States Patent
Kester et al.

(10) Patent No.: US 12,343,428 B2
(45) Date of Patent: Jul. 1, 2025

(54) COMPOSITIONS AND METHODS FOR CANCER TREATMENT

(71) Applicant: University of Virginia Patent Foundation, Charlottesville, VA (US)

(72) Inventors: Mark Kester, Afton, VA (US); Pedro Filipe Da Costa Pinheiro, Charlottesville, VA (US); Jeremy Shaw, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 16/761,114

(22) PCT Filed: Nov. 5, 2018

(86) PCT No.: PCT/US2018/059259
§ 371 (c)(1),
(2) Date: May 1, 2020

(87) PCT Pub. No.: WO2019/090255
PCT Pub. Date: May 9, 2019

(65) Prior Publication Data
US 2020/0268665 A1 Aug. 27, 2020

Related U.S. Application Data

(60) Provisional application No. 62/581,179, filed on Nov. 3, 2017.

(51) Int. Cl.
*A61K 9/1271* (2025.01)
*A61K 31/4174* (2006.01)
*A61K 31/58* (2006.01)
*A61P 35/00* (2006.01)
A61K 31/138 (2006.01)
A61K 31/165 (2006.01)
A61K 45/06 (2006.01)

(52) U.S. Cl.
CPC ........ *A61K 9/1271* (2013.01); *A61K 31/4174* (2013.01); *A61K 31/58* (2013.01); *A61P 35/00* (2018.01); A61K 31/138 (2013.01); A61K 31/165 (2013.01); A61K 45/06 (2013.01)

(58) Field of Classification Search
CPC .. A61K 9/1271; A61K 31/4174; A61K 31/58; A61K 31/138; A61K 31/165; A61K 45/06; A61K 31/4166; A61K 31/517; A61K 31/5377; A61K 31/688; A61P 35/00
See application file for complete search history.

(56) References Cited

U.S. PATENT DOCUMENTS

| | | | |
|---|---|---|---|
| 8,747,891 B2 | 6/2014 | Kester et al. | |
| 9,028,863 B2 | 5/2015 | Kester et al. | |
| 9,326,953 B2 | 5/2016 | Kester et al. | |
| 10,045,953 B2 | 8/2018 | Pearlman et al. | |
| 2003/0026831 A1 | 2/2003 | Lakkaraju et al. | |
| 2005/0025820 A1 | 2/2005 | Kester et al. | |
| 2005/0267060 A1 | 12/2005 | Robertson et al. | |
| 2006/0198882 A1 | 9/2006 | Barenholz et al. | |
| 2007/0031480 A1 | 2/2007 | Mayer et al. | |
| 2008/0008749 A1 | 1/2008 | Pearlman et al. | |
| 2014/0271827 A1 | 9/2014 | Irvine et al. | |
| 2015/0157646 A1 | 6/2015 | Nemeth et al. | |

FOREIGN PATENT DOCUMENTS

| | | |
|---|---|---|
| CN | 104 922 067 | 9/2015 |
| WO | WO 2012/088414 A1 | 6/2012 |
| WO | WO 2012/156437 | 11/2012 |
| WO | WO 2014/144421 | 9/2014 |
| WO | WO 2016/033527 | 3/2016 |
| WO | WO 2017/053990 A1 | 3/2017 |

OTHER PUBLICATIONS

Fedoruk et al., The Prostate 59:77-90 (2004).*
Auzenne et al. (1998) Cytotoxic effects of sphingolipids as single or multi-modality agents on human melanoma and soft tissue sarcoma in vitro. 8 Melanoma Res 227-239.
Mehta et al. (2000) Combined cytotoxic action of paclitaxel and ceramide against the human Tu138 head and neck squamous carcinoma cell line. Cancer Chemother Pharmacol 46:85-92.
Myrick et al. (1999) Paclitaxel-induced apoptosis in Jurkat, a leukemic T cell line, is enhanced by ceramide, Leuk Res 23:569-578.
Stover & Kester (2003) Liposomal Delivery Enhances Short-Chain Ceramide-Induced Apoptosis of Breast Cancer Cells. The Journal of Pharmacology and Experimental Therapeutics, 307(2):468-75.
Adiseshaiah et al. (2013) Synergistic combination therapy with nanoliposomal C6-ceramide and vinblastine is associated with autophagy dysfunction in hepatocarcinoma and colorectal cancer models. Cancer Letters, 2013, vol. 337, No. 2, 254-265.

(Continued)

*Primary Examiner* — Robert S Cabral
(74) *Attorney, Agent, or Firm* — Jenkins, Taylor & Hunt, P.A.

(57) ABSTRACT

Provided are methods for treating cancers and/or tumors in subjects. In some embodiments, the methods include administering to a subject an effective amount of a ceramide nanoliposome (CNL), wherein the CNL has a lipid bilayer that includes one or more $C_2$-$C_{24}$ ceramides and encapsulates one or more anti-cancer and/or anti-tumor agents. Also provided are methods for treating cancers and/or tumors associated with receptor tyrosine kinase or nuclear receptor activities, methods for treating Prostate Cancer, methods for inhibiting growth of EGFR-dependent cancers and/or tumors, methods for inhibiting growth of androgen receptor negative cells, method for reducing or eliminating androgen receptor negative cells from subject, CNLs that encapsulate one or more anti-cancer and/or anti-tumor agents, wherein the CNLs include a lipid bilayer that has one or more $C_2$-$C_{24}$ ceramides, and pharmaceutical compositions that include the disclosed CNLs.

20 Claims, 22 Drawing Sheets

(56) References Cited

OTHER PUBLICATIONS

Aggarwal et al. (2007) Development of abiraterone acetate, a 17-alpha hydroxylase C17,20-lyase inhibitor as a secondary hormonal therapy in prostate cancer. Update on Cancer Therapeutics, vol. 2, No. 4, pp. 171-175.
Barth et al. (2011) Ceramide-Based Therapeutics for the Treatment of Cancer, Anti-Cancer Agents in Medicinal Chemistry, vol. 11, No. 9, pp. 911-919.
Fu et al. (2012) Progress of n1olecular targeted therapies for prostate cancers. BBA—Reviews on Cancer, vol. 1825, No. 2, pp. 140-152.
Morad et al. (2012) Ceramide-Antiestrogen Nanoliposomal Combinations Novel Impact of Hormonal Therapy in Hormone-Insensitive Breast Cancer, Molecular Cancer Therapeutics, vol. 11, No. 11, pp. 2352-2361.
Office Action corresponding to European Patent Application No. 18871955.3 dated Aug. 9, 2021.
Bose et al. (1995) Ceramide Synthase Mediates Daunorubicin-Induced Apoptosis: An Alternative Mechanism for Generating Death Signals. 82 Cell 405-414.
Brizuela et al. (2014) Osteoblast-derived sphingosine 1-phosphate to induce proliferation and confer resistance to therapeutics to bone metastasis-derived prostate cancer cells. 8 Molecular Oncology 1181-1195.
International Preliminary Report on Patentability for PCT/US2018/059259 dated May 20, 2020.
International Search Report for PCT/US2018/059259 dated Jan. 28, 2019.
Mathias et al. (1998) 335 (Pt. 3) Biochem J 465-480.
Notice of Allowance corresponding to U.S. Appl. No. 13/468,578 dated Apr. 7, 2014.
Office Action corresponding to U.S. Appl. No. 13/468,578 dated Feb. 12, 2013.
Office Action corresponding to U.S. Appl. No. 13/468,578 dated Oct. 3, 2013.
Radin (2003) Killing tumours by ceramide-induced apoptosis: a critique of available drugs. 371 (Pt. 2) Biochem J 243-256.
Reddy et al. (2000) Phosphatidylinositol 3-kinase as a mediator of TNF-induced NF-kappa B activation. 164 J Immunol 1355-1363.
Sekine et al. (2011) HDL and sphingosine-1-phosphate activate stat3 in prostate cancer DU145 cells via ERK1/2 and S1P receptors, and promote cell migration and invasion. 71 The Prostate 690-699.
Stover et al. (2005) Systemic Delivery of Liposomal Short-Chain Ceramide Limits Solid Tumor Growth in Murine Models of Breast Adenocarcinoma. Clinical Cancer Research, 11(9):3465-3474.
Strum et al. (1994) 269 J Biol Chem 15493-15497.
Tran et al. (2008) Combining nanoliposomal ceramide with sorafenib synergistically inhibits melanoma and breast cancer cell survival to decrease tumor development. Clinical Cancer Research, 14(11):3571-3581.
Wen et al. (2014) Androgen receptor (AR) positive vs negative roles in prostate cancer cell deaths including apoptosis, anoikis, entosis, necrosis and autophagic cell death. 40 Cancer Treatment Reviews 31-40.
Written Opinion of the International Searching Authority for PCT/US2018/059259 dated Jan. 28, 2019.
Chandrasekar et al.,2015 "Mechanisms of resistance in castration resistant prostate cancer (CRPC)" Transl Androl Urol, 4(3): pp. 365-380.
Feng et al., 2019 "Androgen Receptor Signaling in the Development of Castration-Resistant Prostate Cancer," Frontiers in Oncology, vol. 9, 858; 10 Pages.
Rathkopf et al., 2013 "Androgen Receptor Antagonists in Castration Resistant Prostate Cancer," Cancer J.19; pp. 43-49.
Scher et al., 2004 "Targeting the androgen receptor: improving outcomes for castration-resistant prostate cancer," Endocrine-Related Cancer, 11, pp. 459-476.
Fedoruk, M.N., et al., "P-Glycoprotein Increases the Efflux of the Androgen Dihydrotestosterone and Reduces Androgen Responsive Gene Activity in Prostate Tumor Cells", The Prostate, vol. 59, 2004, pp. 77-90.

\* cited by examiner

COMPOSITIONS AND METHODS FOR CANCER TREATMENT

CROSS-REFERENCE TO RELATED APPLICATION

This application claims the benefit of U.S. Provisional Patent Application Ser. No. 62/581,179, filed Nov. 3, 2017, the disclosure of which is incorporated herein by reference in its entirety.

TECHNICAL FIELD

The presently disclosed subject matter relates to compositions and methods for cancer treatment. In some embodiments, the presently disclosed subject matter relates to compositions comprising nanoliposomes encapsulating and/or coated by one or more $C_2$-$C_{24}$ ceramides and their use alone or in combination with one or more additional anti-cancer and/or anti-tumor therapies for cancer treatment.

BACKGROUND

Sphingolipids present in biological membranes have been shown to have various biological activities on cell functions such as modulating growth and differentiation. Ceramides, which are present in cell membranes, are a family of lipid molecules that are made up of a sphingosine and a fatty. Among the biological functions of ceramides is a connection between ceramides and apoptosis, including apoptosis in tumor and cancer cells. As such, it is possible that enhancing intracellular ceramides can result in apoptosis such as, for example, during anti-tumor and/or anti-cancer therapy (see e.g., Bose et al., 1995; Mathias et al., 1998).

Short chain ceramides such as $C_2$- or $C_6$-ceramides have been shown to have anti-cancer activities in vitro (see e.g., Radin, 2003), including melanoma and soft tissue sarcoma (Auzenne et al., 1998), Jurkat leukemia cells (Myrick et al., 1999), and head and neck squamous cancer (Mehta et al., 2000) cell lines. In vivo, ceramides $C_2$, $C_6$ and their analogues have also been shown to induce cell cycle arrest in a variety of tumor types (reviewed in Mathias et al., 1998), and endogenous ceramide production has been shown to mediate apoptosis induced by a variety of anti-cancer drugs (Mathias et al., 1998) including daunorubicin (Reddy et al., 2000), doxorubicin (Lucci et al., 1999), ara-C (Strum et al., 1994), and paclitaxel (Charles et al., 2001).

Prostate Cancer (PCa) is one of the most incident cancers in men, and is estimated to account for 19% of the newly diagnosed cases and 9% of cancer-related deaths in 2018 in the United States alone. By the year of 2020, PCa is estimated to have a cost of care around $16 billion just in the United States, the third highest for any tumor. These figures argue that both the epidemiologic and economic burden for PCa will increase in the near future as screening methods and an aging population will lead to more diagnosed cases. Despite its high incidence in men and extensive research efforts, the treatment of PCa remains elusive, mainly due to its heterogeneity and complex progression.

The prostate is an exocrine gland that depends on male hormones (androgens, such as testosterone) that upon binding to the Androgen Receptor (AR) lead to normal development and growth of this organ. In the early 1940s, it was reported that PCa cells are also responsive to these hormones, and from that point on androgen deprivation therapy (ADT) became the gold standard for PCa treatment. ADT by either surgical castration or anti-androgens (blocking of androgen synthesis or AR antagonists) leads to remission in 70-80% of patients, however, 18-24 months virtually all patients relapse to a highly aggressive stage of PCa, castration-resistant prostate cancer (CRPC). CRPC is responsible for the vast majority of PCa-related deaths. Therefore, it is crucial to develop novel treatment options for PCa patients that are more efficient than traditional ADT.

Similarly, Head and Neck Squamous Cell Carcinoma (HNSCC), which refers to cancers arising mainly in the lip and oral cavity, pharynx, and larynx, is the $7^{th}$ most common cancer worldwide. HNSCC had over 686,000 cases diagnosed in 2012, which yielded only a 61% 5-year survival rate. Current conventional treatment options include chemotherapy, radiation, and surgery, which can leave patients permanently disfigured. In addition to the terrible burden on patients who suffer from this disease, it is also a financial burden in that treatment of HNSCC is set to cost $4.34 billion in the United States alone by 2020.

Unfortunately, despite the large volume of cases and poor outcomes for patients, only one targeted therapy exists for HNSCC. Cetuximab, a monoclonal antibody which binds to the active site of the Epidermal Growth Factor Receptor (EGFR) blocking its activity, is the sole targeted therapy that has shown even modest clinical efficacy in HNSCC. EGFR has been identified as a druggable target in HNSCC because it is overexpressed in 40-80% of tumors. In the same vein, two other drugs which inhibit EGFR signaling, Erlotinib and Gefitinib, have also been tested for efficacy in treating HNSCC. However, after showing promise in phase I and phase II clinical trials, both drugs failed phase III. This was particularly counterintuitive as both Erlotinib and Gefitinib were successful therapies for EGFR-dependent lung cancer.

What are needed, therefore, are new compositions and methods for treating cancers and/or tumors, particularly PCa and HNSCC.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides methods for treating cancers and/or tumors in a subject. In some embodiments, the methods comprise administering to the subject an effective amount of a ceramide nanoliposome (CNL), wherein the CNL comprises a lipid bilayer comprising one or more $C_2$-$C_{24}$ ceramides and encapsulates one or more anti-cancer and/or anti-tumor agents. In some embodiments, the cancer and/or the tumor is selected from the group consisting of Prostate Cancer (PCa), optionally Androgen-resistant Prostate Cancer (ARPCa), Head and Neck Squamous Cell Carcinoma (HNSCC), Non-Small Cell Lung Cancer (NSCLC), Breast Cancer, Colorectal Cancer, Gastric Cancer, Esophageal Cancer, Ovarian Cancer, and Biliary Tract Cancer, or comprises a metastatic cell derived therefrom. In some embodiments, the cancer and/or the tumor is prostate cancer (PCa), optionally an Androgen-resistant Prostate Cancer (ARPCa). In some embodiments, the lipid bilayer of the CNL comprises a $C_6$ ceramide. In some embodiments, the subject is a mammal, optionally a human.

In some embodiments, the presently disclosed subject matter methods further comprise administering to the subject a second anti-cancer and/or anti-tumor therapy selected from the group consisting of radiotherapy, surgery, an androgen deprivation therapy, an anti-androgen synthesis therapy, an estrogen deprivation therapy, an anti-estrogen synthesis therapy, a receptor tyrosine kinase inhibitor therapy, and a nuclear receptor inhibitor therapy. In some embodiments, the second anti-cancer and/or anti-tumor therapy is administered to the subject prior to, concurrently with, or subsequent to administering the effective amount of the CNL to the subject. In some embodiments, the anti-androgen synthesis therapy comprises administering an inhibitor of androgen synthesis and/or androgen receptor (AR) signaling, optionally wherein the inhibitor is an inhibitor of a CYP17A1 biological activity and/or an AR antagonist. In some embodiments, the inhibitor of a CYP17A1 biological activity and/or the AR antagonist is selected from the group consisting of abiraterone acetate and enzalutamide. In some embodiments, the anti-androgen synthesis therapy comprises administering an inhibitor of androgen synthesis and/or androgen receptor (AR) signaling, optionally wherein the inhibitor is abiraterone acetate and enzalutamide, and/or an analog thereof, or is an antibody that binds to an AR or is a paratope-containing fragment or derivative thereof. In some embodiments, the anti-estrogen synthesis therapy comprises administering an inhibitor of estrogen synthesis and/or estrogen receptor (ER) signaling, optionally wherein the inhibitor is tamoxifen, raloxifene, toremifene, and/or an analog thereof, or is an antibody that binds to an ER or is a paratope-containing fragment or derivative thereof. In some embodiments, the second anti-cancer and/or anti-tumor therapy comprises administering a receptor tyrosine kinase inhibitor to the subject. In some embodiments, the receptor tyrosine kinase inhibitor is an epidermal growth factor receptor (EGFR) inhibitor. In some embodiments, the EGFR inhibitor is selected from the group consisting of gefitinib, erlotinib, afatinib, lapatinib, neratinib, canertinib, pelitinib, sapitinib, osimertinib, varlitinib, icotinib, and analogues thereof, or is an anti-EGFR antibody or a paratope-containing fragment or derivative thereof, optionally wherein the anti-EGFR antibody is selected from the group consisting of trastuzumab, cetuximab, panitumumab, pertuzumab, and matuzumab. In some embodiments, the anti-EGFR antibody is selected from the group consisting of trastuzumab, cetuximab, panitumumab, pertuzumab, and matuzumab, or is a paratope-containing fragment or derivative thereof. In some embodiments, the second anti-cancer and/or anti-tumor therapy comprises administering a nuclear receptor inhibitor to the subject. In some embodiments, the nuclear receptor inhibitor is an androgen receptor (AR) antagonist, an estrogen receptor (ER) antagonist, or a combination thereof. In some embodiments, the nuclear receptor inhibitor is selected from the group consisting of abiraterone acetate, enzalutamide, tamoxifen, raloxifene, toremifene, and/or an analog thereof, or is an antibody or a paratope-containing fragment or derivative thereof that binds to an AR or and ER. In some embodiments, the subject is a mammal, optionally a human.

The presently disclosed subject matter also provides in some embodiments methods for treating cancers and/or tumors associated with activity of a receptor tyrosine kinase or a nuclear receptor in a subject. In some embodiments, the methods comprise administering to the subject an effective amount of a ceramide nanoliposome (CNL), wherein the CNL comprises a lipid bilayer comprising one or more $C_2$-$C_{24}$ ceramides and encapsulates one or more nuclear receptor inhibitors, one or more tyrosine kinase inhibitors, or a combination thereof. In some embodiments, the cancer and/or the tumor is selected from the group consisting of Prostate Cancer (PCa), optionally Androgen-resistant Prostate Cancer (ARPCa), Head and Neck Squamous Cell Carcinoma (HNSCC), Non-Small Cell Lung Cancer (NSCLC), Breast Cancer, Colorectal Cancer, Gastric Cancer, Esophageal Cancer, Ovarian Cancer, and Biliary Tract Cancer, or comprises a metastatic cell derived therefrom. In some embodiments, the cancer and/or the tumor is prostate cancer (PCa), optionally an Androgen-resistant Prostate Cancer (ARPCa). In some embodiments, the lipid bilayer of the CNL comprises a $C_6$ ceramide. In some embodiments, the subject is a mammal, optionally a human.

In some embodiments, the presently disclosed methods further comprise administering to the subject a second anti-cancer and/or anti-tumor therapy selected from the group consisting of radiotherapy, surgery, an androgen deprivation therapy, an anti-androgen synthesis therapy, an estrogen deprivation therapy, an anti-estrogen synthesis therapy, a receptor tyrosine kinase inhibitor therapy, and a nuclear receptor inhibitor therapy. In some embodiments, the second anti-cancer and/or anti-tumor therapy is administered to the subject prior to, concurrently with, or subsequent to administering the effective amount of the CNL to the subject. In some embodiments, the anti-androgen synthesis therapy comprises administering an inhibitor of androgen synthesis and/or androgen receptor (AR) signaling, optionally wherein the inhibitor is an inhibitor of a CYP17A1 biological activity and/or an AR antagonist. In some embodiments, the inhibitor of a CYP17A1 biological activity and/or the AR antagonist is selected from the group consisting of abiraterone acetate and enzalutamide. In some embodiments, the anti-androgen synthesis therapy comprises administering an inhibitor of androgen synthesis and/or androgen receptor (AR) signaling, optionally wherein the inhibitor is abiraterone acetate and enzalutamide, and/or an analog thereof, or is an antibody that binds to an AR or is a paratope-containing fragment or derivative thereof. In some embodiments, the anti-estrogen synthesis therapy comprises administering an inhibitor of estrogen synthesis and/or estrogen receptor (ER) signaling, optionally wherein the inhibitor is tamoxifen, raloxifene, toremifene, and/or an analog thereof, or is an antibody that binds to an ER or is a paratope-containing fragment or derivative thereof. In some embodiments, the second anti-cancer and/or anti-tumor therapy comprises administering a receptor tyrosine kinase inhibitor to the subject. In some embodiments, the receptor tyrosine kinase inhibitor is an epidermal growth factor receptor (EGFR) inhibitor. In some embodiments, the EGFR inhibitor is selected from the group consisting of gefitinib, erlotinib, afatinib, lapatinib, neratinib, canertinib, pelitinib, sapitinib, osimertinib, varlitinib, icotinib, and analogues thereof, or is an anti-EGFR antibody or a paratope-containing fragment or derivative thereof, optionally wherein the anti-EGFR antibody is selected from the group consisting of trastuzumab, cetuximab, panitumumab, pertuzumab, and matuzumab. In some embodiments, the anti-EGFR antibody is selected from the group consisting of trastuzumab, cetuximab, panitumumab, pertuzumab, and matuzumab, or is a paratope-containing fragment or derivative thereof. In some embodiments, the second anti-cancer and/or anti-tumor therapy comprises administering a nuclear receptor inhibitor to the subject. In some embodiments, the nuclear receptor inhibitor is an androgen receptor (AR) antagonist, an estrogen receptor (ER) antagonist, or a combination thereof. In some embodiments, the nuclear receptor inhibitor is selected from the group consisting of abiraterone acetate, enzalutamide, tamoxifen, raloxifene, toremifene, and/or an analog thereof, or is an antibody or a paratope-containing fragment or derivative thereof that binds to an AR or and ER. In some embodiments, the subject is a mammal, optionally a human.

In some embodiments, the presently disclosed subject matter provides methods for treating Prostate Cancer (PCa) in a subject. In some embodiments, the methods comprise administering to the subject an effective amount of a ceramide nanoliposome (CNL), wherein the CNL comprises a lipid bilayer comprising one or more $C_2$-$C_{24}$ ceramides and encapsulates one or more anti-cancer and/or anti-tumor agents. In some embodiments, the lipid bilayer of the CNL comprises a $C_6$ ceramide. In some embodiments, the subject is a mammal, optionally a human.

In some embodiments, the presently disclosed methods further comprise administering to the subject a second anti-cancer and/or anti-tumor therapy selected from the group consisting of radiotherapy, surgery, an androgen deprivation therapy, an anti-androgen synthesis therapy, and a nuclear receptor inhibitor therapy. In some embodiments, the second anti-cancer and/or anti-tumor therapy is administered to the subject prior to, concurrently with, or subsequent to administering the effective amount of the CNL to the subject. In some embodiments, the anti-androgen synthesis therapy comprises administering an inhibitor of androgen synthesis and/or androgen receptor (AR) signaling, optionally wherein the inhibitor is abiraterone acetate and enzalutamide, and/or an analog thereof, or is an antibody that binds to an AR or is a paratope-containing fragment or derivative thereof. In some embodiments, the inhibitor of androgen synthesis and/or androgen receptor (AR) signaling comprises an inhibitor of a CYP17A1 biological activity and/or an AR antagonist. In some embodiments, the inhibitor of a CYP17A1 biological activity and/or the AR antagonist is selected from the group consisting of abiraterone acetate and enzalutamide. In some embodiments, the subject is a mammal, optionally a human.

The presently disclosed subject matter also provides in some embodiments methods for inhibiting growth of EGFR-dependent cancers and/or tumors. In some embodiments, the methods comprise contacting the EGFR-dependent cancer or tumor with an effective amount of a ceramide nanoliposome (CNL), wherein the CNL comprises a lipid bilayer comprising one or more $C_2$-$C_{24}$ ceramides and encapsulates one or more anti-cancer and/or anti-tumor agents. In some embodiments, the EGFR-dependent cancer and/or tumor is selected from the group consisting of Head and Neck Squamous Cell Carcinoma (HNSCC), Non-Small Cell Lung Cancer (NSCLC), Breast Cancer, Colorectal Cancer, Gastric Cancer, Esophageal Cancer, Ovarian Cancer, and Biliary Tract Cancer, or is a metastasis therefrom. In some embodiments, the EGFR-dependent cancer and/or tumor is present within a subject. In some embodiments, the one or more anti-cancer and/or anti-tumor agents comprises an inhibitor of epidermal growth factor receptor (EGFR) signaling. In some embodiments, the inhibitor of EGFR signaling is selected from the group consisting of gefitinib, erlotinib, afatinib, lapatinib, neratinib, canertinib, pelitinib, sapitinib, osimertinib, varlitinib, icotinib, and analogues thereof, and/or is an anti-EGFR antibody or a paratope-containing fragment or derivative thereof, optionally wherein the anti-EGFR antibody is selected from the group consisting of trastuzumab, cetuximab, panitumumab, pertuzumab, and matuzumab. In some embodiments, the subject is a mammal, optionally a human.

In some embodiments, the presently disclosed methods further comprise administering to the subject a second anti-cancer and/or anti-tumor therapy selected from the group consisting of radiotherapy, surgery, and a EGFR inhibitor, or any combination thereof. In some embodiments, the second anti-cancer and/or anti-tumor therapy is administered to the subject prior to, concurrently with, or subsequent to administering the effective amount of the CNL to the subject. In some embodiments, the subject is a mammal, optionally a human.

In some embodiments, the presently disclosed subject matter also provides methods for inhibiting growth of androgen receptor (AR) negative cells. In some embodiments, the methods comprise contacting the AR negative cell with an effective amount of a ceramide nanoliposome (CNL), wherein the CNL comprises a lipid bilayer comprising one or more $C_2$-$C_{24}$ ceramides and encapsulates one or more anti-cancer and/or anti-tumor agents. In some embodiments, the AR negative cell is present within a subject, optionally within the prostate of the subject. In some embodiments, the presently disclosed method further comprises administering an effective amount of the CNL to the subject. In some embodiments, the subject is a mammal, optionally a human. In some embodiments, the presently disclosed methods further comprise contacting the AR negative cell with an inhibitor of androgen synthesis and/or an inhibitor of androgen receptor (AR) signaling. In some embodiments, the inhibitor of androgen synthesis and/or an inhibitor of androgen receptor (AR) signaling is an inhibitor of a CYP17A1 biological activity, an AR antagonist, or a combination thereof. In some embodiments, the inhibitor of a CYP17A1 biological activity and/or the AR antagonist is selected from the group consisting of abiraterone acetate and enzalutamide.

In some embodiments, the presently disclosed methods further comprise administering to the subject a second anti-cancer and/or anti-tumor therapy, wherein the second anti-cancer and/or anti-tumor therapy comprises radiotherapy, surgery, an androgen deprivation therapy, to an anti-androgen synthesis therapy, an anti-androgen receptor (AR) signaling therapy, or any combination thereof, and further wherein the second anti-cancer and/or anti-tumor therapy is administered to the subject prior to, concurrently with, or subsequent to administering the effective amount of the CNL to the subject. In some embodiments, the subject is a mammal, optionally a human. In some embodiments, the second anti-cancer and/or anti-tumor therapy comprises treatment with abiraterone acetate and/or enzalutamide, analogues thereof, or is an anti-AR antibody or a paratope-containing fragment or derivative thereof.

The presently disclosed subject matter also provides in some embodiments methods for reducing or eliminating androgen receptor (AR) negative cells from a subject's prostate. In some embodiments, the methods comprise administering to the subject an effective amount of a ceramide nanoliposome (CNL) comprising a lipid bilayer comprising one or more $C_2$-$C_{24}$ ceramides and encapsulating one or more anti-cancer and/or anti-tumor agents, wherein the CNL contacts the AR negative cells and induces apoptosis thereof. In some embodiments, the presently disclosed methods further comprise administering to the subject an effective amount of an inhibitor of androgen synthesis and/or androgen receptor (AR) signaling. In some embodiments, the inhibitor of androgen synthesis and/or androgen receptor (AR) signaling is an inhibitor of a CYP17A1 biological activity and/or an AR antagonist, optionally selected from the group consisting of abiraterone acetate and enzalutamide. In some embodiments, the subject is a mammal, optionally a human.

In some embodiments, the presently disclosed subject matter also provides ceramide nanoliposomes (CNLs) encapsulating one or more anti-cancer and/or anti-tumor agents. In some embodiments, the ceramide nanoliposome comprises a lipid bilayer comprising one or more $C_2$-$C_{24}$ ceramides and the one or more anti-cancer and/or anti-tumor agents are selected from the group consisting of tyrosine kinase receptor inhibitors and nuclear receptor inhibitors. In some embodiments, the lipid bilayer of the CNL comprises a $C_6$ ceramide. In some embodiments, the CNLs of the presently disclosed subject matter further comprise one or more pharmaceutically acceptable carriers or diluents. In some embodiments, the one or more anti-cancer and/or anti-tumor agents are selected from the group consisting of a receptor tyrosine kinase inhibitor and a nuclear receptor inhibitor, or a combination thereof. In some embodiments, the receptor tyrosine kinase inhibitor is an epidermal growth factor receptor (EGFR) inhibitor. In some embodiments, the EGFR inhibitor is selected from the group consisting of gefitinib, erlotinib, afatinib, lapatinib, neratinib, canertinib, pelitinib, sapitinib, osimertinib, varlitinib, icotinib, and analogues thereof, or is an anti-EGFR antibody or a paratope-containing fragment or derivative thereof, optionally wherein the anti-EGFR antibody is selected from the group consisting of trastuzumab, cetuximab, panitumumab, pertuzumab, and matuzumab. In some embodiments, the nuclear receptor inhibitor is an inhibitor of a CYP17A1 biological activity and/or is an AR antagonist. In some embodiments, the inhibitor of a CYP17A1 biological activity and/or the AR antagonist is selected from the group consisting of abiraterone acetate and enzalutamide.

In some embodiments, the presently disclosed subject matter also provides pharmaceutical compositions comprising the CNLs disclosed herein and one or more pharmaceutically acceptable carriers or diluents. In some embodiments, the pharmaceutical composition is pharmaceutically acceptable for use in a human.

Thus, it is an object of the presently disclosed subject matter to provide compositions and methods for use in treating cancers and/or tumors.

An object of the presently disclosed subject matter having been stated hereinabove, and which is achieved in whole or in part by the compositions and methods disclosed herein, other objects will become evident as the description proceeds when taken in connection with the accompanying Figures as best described herein below.

BRIEF DESCRIPTION OF THE FIGURES

FIG. 2A presents data for AR negative PC-3 cells, and FIG. 2B presents data for AR positive LNCaP cells. In each of FIGS. 2A and 2B, the leftmost bar of each triad corresponds a negative control (0 µM CNL), the middle bar corresponds to 5 µM CNL treatment, and the rightmost bar corresponds to 10 µM CNL treatment. The error bars correspond to one (1) standard deviation, and the asterisks indicate differences that are significant at $p<0.05$.

FIG. 4A) or enzalutamide (Enza or MDV; FIG. 4B) had a synergistic effect in reducing cell viability in AR positive LNCaP cells as measured by flow cytometry. The leftmost bars in FIGS. 4A and 4B show viabilities of LNCaP cells after 72 hours of treatment with 20 µM CNL alone. The middle bars in FIGS. 4A and 4B show viabilities of LNCaP cells after 72 hours of treatment with 20 µM abiraterone acetate (FIG. 4A) or 30 µM enzalutamide (FIG. 4B) alone. The rightmost bars in FIGS. 4A and 4B show viabilities of LNCaP cells after 72 hours of treatment with 20 µM CNL+20 µM abiraterone acetate (FIG. 4A) or 20 µM CNL+30 µM enzalutamide (FIG. 4B). The error bars correspond to one (1) standard deviation.

FIG. 5A) and CNL or the degree of symmetry between CNL and enzalutamide (MDV3100; FIG. 5B). As shown in FIGS. 5A and 5B, whereas certain combinations of abiraterone acetate and CNL showed either synergy or antagonism, all tested combinations of CNL and enzalutamide showed some degree of synergy.

FIG. 6A is a bar graph showing $C_6$ ceramide levels (pmol/mg total protein) and FIG. 6B is a bar graph showing total ceramide levels (pmol/mg total protein) at 1, 12, 24, and 48 hours after exposure to a negative control (first bar of each quartet), 10 µM abiraterone acetate alone (second bar of each quartet), 10 µM CNL alone (third bar of each quartet), and 10 µM abiraterone acetate plus 10 µM CNL (fourth bar of each quartet). It is noted that In FIG. 6A, the negative control and 10 µM abiraterone acetate alone levels were too low to be depicted in the Figure. Bar graphs represent data of five (5) replicates. The error bars correspond to one (1) standard deviation.

FIG. 7A is a bar graph showing viability of UNC-10 HNSCC cells exposed to the EGFRi Erlotinib at 0 µM, 0.5 µM, 1 µM, 5 µM, 10 µM, and 25 µM after 24 hours. FIG. 7B is a bar graph showing viability of UNC-10 HNSCC cells exposed to the EGFRi Erlotinib at 0 µM, 0.5 µM, 1 µM, 5 µM, 10 µM, and 25 µM after 48 hours. FIG. 7C is a bar graph showing viability of SCC-25 HNSCC cells exposed to the EGFRi Erlotinib at 0 µM, 0.5 µM, 1 µM, 5 µM, 10 µM, and 25 µM after 24 hours. FIG. 7D is a bar graph showing viability of SCC-25 HNSCC cells exposed to the EGFRi Erlotinib at 0 µM, 0.5 µM, 1 µM, 5 µM, 10 µM, and 25 µM Erlotinib after 48 hours. The error bars correspond to one (1) standard deviation.

FIG. 8A is a bar graph showing viability of UNC-10 HNSCC cells exposed to the EGFRi Gefitinib at 0 µM, 0.5 µM, 1 µM, 5 µM, 10 µM, and 25 µM after 24 hours. FIG. 8B is a bar graph showing viability of UNC-10 HNSCC cells exposed to the EGFRi Gefitinib at 0 µM, 0.5 µM, 1 µM, 5 µM, 10 µM, and 25 µM after 48 hours. FIG. 8C is a bar graph showing viability of SCC-25 HNSCC cells exposed to the EGFRi Gefitinib at 0 µM, 0.5 µM, 1 µM, 5 µM, 10 µM, and 25 µM after 24 hours. FIG. 8D is a bar graph showing viability of SCC-25 HNSCC cells exposed to the EGFRi Gefitinib at 0 µM, 0.5 µM, 1 µM, 5 µM, 10 µM, and 25 µM after 48 hours. The error bars correspond to one (1) standard deviation.

FIG. 9A is a bar graph showing viability of UNC-10 HNSCC cells exposed to CNL at 0 µM, 2.5 µM, 5 µM, 10 µM, and 25 µM after 24 hours. FIG. 9B is a bar graph showing viability of UNC-10 HNSCC cells exposed to CNL at 0 µM, 2.5 µM, 5 µM, 10 µM, and 25 µM after 48 hours. FIG. 9C is a bar graph showing viability of SCC-25 HNSCC cells exposed to CNL at 0 µM, 2.5 µM, 5 µM, 10 µM, and 25 µM after 24 hours. FIG. 9D is a bar graph showing viability of SCC-25 HNSCC cells exposed to CNL at 0 µM, 2.5 µM, 5 µM, 10 µM, and 25 µM after 48 hours. The error bars correspond to one (1) standard deviation.

FIG. 10A is a series of bar graph showing viability of UNC-10 HNSCC cells exposed to CNL at 0 µM, 2.5 µM, 5 µM, 10 µM, and 25 µM (left to right in each quintet) and/or EGFRi 1 at 0 µM, 5 µM, 10 µM, and 25 µM after 24 hours. FIG. 10B is a series of bar graph showing viability of UNC-10 HNSCC cells exposed to CNL at 0 µM, 2.5 µM, 5 µM, 10 µM, and 25 µM (left to right in each quintet) and/or EGFRi 1 at 0 µM, 5 µM, 10 µM, and 25 µM after 48 hours. FIG. 10C is a series of bar graph showing viability of SCC-25 HNSCC cells exposed to CNL at 0 µM, 2.5 µM, 5 µM, 10 µM, and 25 µM (left to right in each quintet) and/or EGFRi 1 at 0 µM, 5 µM, 10 µM, and 25 µM after 24 hours. FIG. 10D is a series of bar graph showing viability of SCC-25 HNSCC cells exposed to CNL at 0 µM, 2.5 µM, 5 µM, 10 µM, and 25 µM (left to right in each quintet) and/or EGFRi 1 at 0 µM, 5 µM, 10 µM, and 25 µM after 48 hours. The error bars correspond to one (1) standard deviation.

FIG. 11A is a series of bar graph showing viability of UNC-10 HNSCC cells exposed to CNL at 0 µM, 2.5 µM, 5 µM, 10 µM, and 25 µM (left to right in each quintet) and/or EGFRi 2 at 0 µM, 5 µM, 10 µM, and 25 µM after 24 hours. FIG. 11B is a series of bar graph showing viability of UNC-10 HNSCC cells exposed to CNL at 0 µM, 2.5 µM, 5 µM, 10 µM, and 25 µM (left to right in each quintet) and/or EGFRi 2 at 0 µM, 5 µM, 10 µM, and 25 µM after 48 hours. FIG. 11C is a series of bar graph showing viability of SCC-25 HNSCC cells exposed to CNL at 0 µM, 2.5 µM, 5 µM, 10 µM, and 25 µM (left to right in each quintet) and/or EGFRi 2 at 0 µM, 5 µM, 10 µM, and 25 µM after 24 hours. FIG. 11D is a series of bar graph showing viability of SCC-25 HNSCC cells exposed to CNL at 0 µM, 2.5 µM, 5 µM, 10 µM, and 25 µM (left to right in each quintet) and/or EGFRi 2 at 0 µM, 5 µM, 10 µM, and 25 µM after 48 hours. The error bars correspond to one (1) standard deviation.

FIG. 12A is a series of bar graph showing viability of UNC-10 HNSCC cells exposed to CNL at 0 µM (Ghost), 2.5 µM, or 5 µM (left to right in each triad) and/or Erlotinib at 0 µM (DMSO vehicle negative control), 10 µM, and 25 µM. FIG. 12B is a series of bar graph showing viability of UNC-10 HNSCC cells exposed to CNL at 0 µM (Ghost), 2.5 µM, or 5 µM (left to right in each triad) and/or Gefitinib at 0 µM (DMSO vehicle negative control), 10 µM, and 25 µM. FIG. 12C is a series of bar graph showing viability of SCC-25 HNSCC cells exposed to CNL at 0 µM (Ghost), 2.5 µM, or 5 µM (left to right in each triad) and/or Erlotinib at 0 µM (DMSO vehicle negative control), 10 µM, and 25 µM. FIG. 12D is a series of bar graph showing viability of SCC-25 HNSCC cells exposed to CNL at 0 µM (Ghost), 2.5 µM, or 5 µM (left to right in each triad) and/or Gefitinib at 0 µM (DMSO vehicle negative control), 10 µM, and 25 µM. The error bars correspond to one (1) standard deviation.

DETAILED DESCRIPTION

I. Definitions

Figure 1:
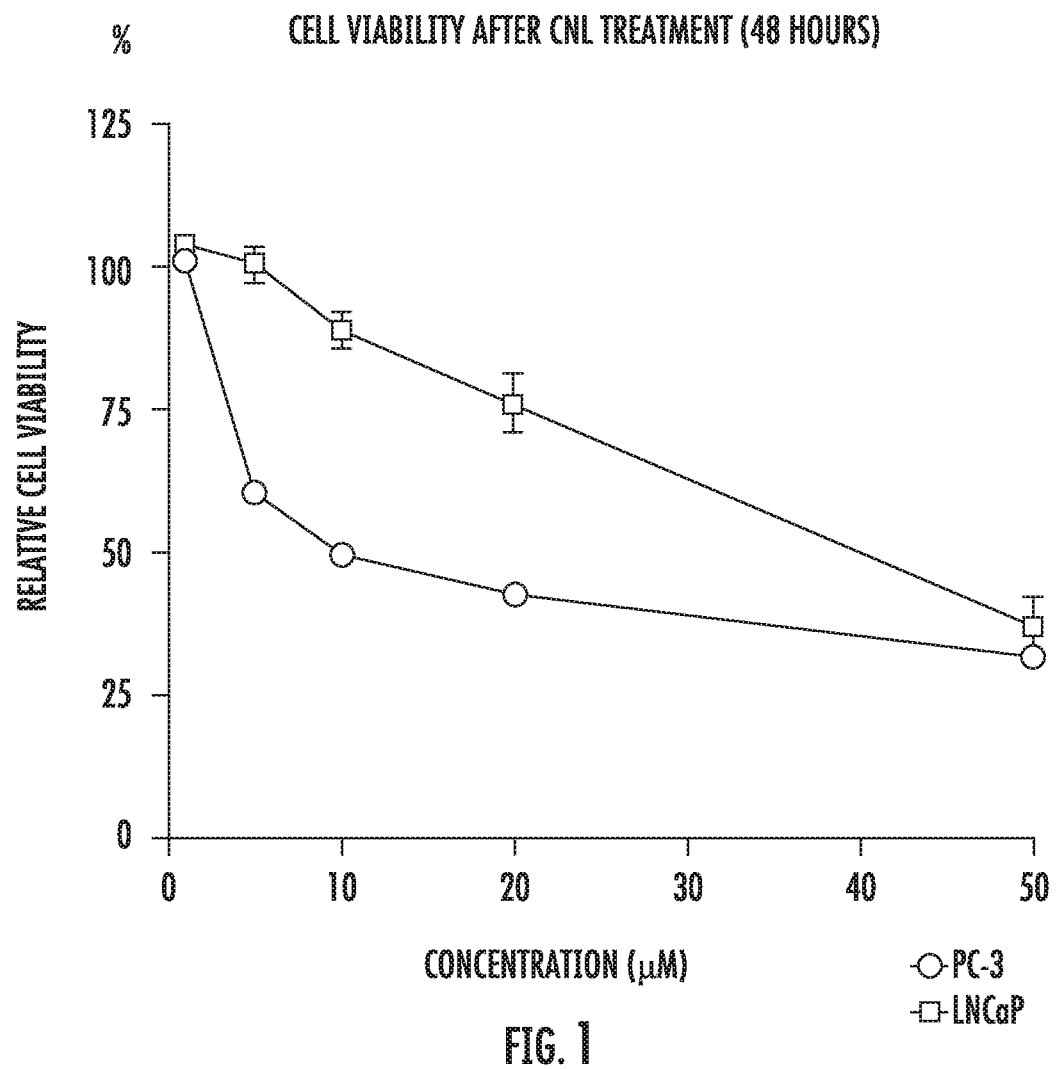
FIG. 1 is a graph showing viability of AR negative PC-3 prostate cancer cells and AR positive LNCaP prostate cancer cells after 48 hours of treatment with a NanoLiposome formulation that includes $C_6$ ceramide (CNL) at 1 µM, 5 µM, 10 µM, 20 µM, and 50 µM. ■: AR negative PC-3 cells. ●: AR positive LNCaP cells. The error bars correspond to one (1) standard deviation.

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed and claimed subject matter.

Following long-standing patent law convention, the terms "a", "an", and "the" refer to "one or more" when used in this application, including in the claims. For example, the phrase "an antibody" refers to one or more antibodies, including a plurality of the same antibody. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent(s) present in the pharmaceutical composition. It is noted, however, that carriers, excipients, and/or other inactive agents can and likely would be present in such a pharmaceutical composition and are encompassed within the nature of the phrase "consisting essentially of".

With respect to the terms "comprising", "consisting of", and "consisting essentially of", where one of these three terms is used herein, the presently disclosed and claimed subject matter can include the use of either of the other two terms. For example, in some embodiments, the presently disclosed subject matter relates to compositions comprising antibodies. It would be understood by one of ordinary skill in the art after review of the instant disclosure that the presently disclosed subject matter thus encompasses compositions that consist essentially of the antibodies of the presently disclosed subject matter, as well as compositions that consist of the antibodies of the presently disclosed subject matter.

As used herein, the terms "condition", "disease condition", "disease", "disease state", and "disorder" refer to physiological states in which diseased cells can be targeted with the compositions and methods of the presently disclosed subject matter. In some embodiments, a condition, disease condition, disease, disease state, and/or disorder that can be targeted with the compositions and methods of the presently disclosed subject matter is a tumor and/or a cancer, and/or a cell derived therefrom. Any such disease, disorder, or condition responsive to the compositions and methods of the presently disclosed subject matter can be treated, and/or a symptom thereof can be ameliorated, using the compositions and methods of the presently disclosed subject matter.

As used herein, the term "mammal" refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The term "subject" as used herein refers to a member of any invertebrate or vertebrate species. Accordingly, the term "subject" is intended to encompass in some embodiments any member of the Kingdom Animalia including particularly the Class Mammalia (mammals) and all Orders and Families encompassed therein. Thus, in some embodiments the presently disclosed subject matter concerns mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses.

As used herein, the phrase "therapeutic agent" refers to an agent that is used to, for example, treat, inhibit, prevent, mitigate the effects of, reduce the severity of, reduce the likelihood of developing, slow the progression of, and/or cure, a disease or disorder.

The terms "treatment" and "treating" as used herein refer to both therapeutic treatment and prophylactic or preventative measures, wherein the object is to prevent or slow down (lessen) the targeted pathologic condition, prevent the pathologic condition, pursue or obtain beneficial results, and/or lower the chances of the individual developing a condition, disease, or disorder, even if the treatment is ultimately unsuccessful. Those in need of treatment include those already with the condition as well as those prone to have or predisposed to having a condition, disease, or disorder, or those in whom the condition is to be prevented.

As used herein, the term "tumor" refers to any neoplastic cell growth and/or proliferation, whether malignant or benign, and all pre-cancerous and cancerous cells and tissues. The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas, and meningiomas). As used herein, the terms "cancer and "tumor" are also intended to refer to multicellular tumors as well as individual neoplastic or pre-neoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, breast, ovary, colon, or rectum, and/or a metastatic cell derived therefrom.

As used herein, the phrase "EGFR inhibitor" refers to an inhibitor of signaling through the epidermal growth factor receptor (EGFR), in some embodiments a mammalian or human EGFR. In some embodiments, an EGFR inhibitor is an antibody such as ERBITUX™ brand (cetuximab; Eli Lilly and Company, Indianapolis, Indiana, United States of America) and ABX-EGF/VECTIBIX® (panitumumab; Amgen, Inc., Thousand Oaks, California, United States of America). In some embodiments, an EGFR inhibitor is a small molecule that competes with ATP such as TARCEVA® (Erlotinib; OSI Pharmaceuticals, Inc., Melville, New York, United States of America), IRESSA® (Gefitinib, AstraZeneca plc, Cambridge, England), tyrphostins (see Dvir et al., 1991), tricyclic pyrimidine compounds disclosed in U.S. Pat. No. 5,679,683; and PD166285 (6-(2,6-dichlorophenyl)-2-(4-(2-diethylaminoethoxy) phenylamino)-8-methyl-8H-pyrido(2,3-d)pyrimidin-7-one; Panek et al., 1997.

As used herein, the phrases "increasing apoptosis", "enhancing apoptosis", "inducing apoptosis", and the like are defined as an increase in the rate of programmed cell death, i.e. more cells are induced into the death process as compared to exposure (contact with) either gemcitabine alone or the ceramide alone. Increasing apoptosis also includes the inhibition of cell division which results in a decrease in the total number of viable cancer cells.

As used herein, the term "inhibiting cancer" or "inhibiting cancer cell growth" is intended to include the inhibition of undesirable or inappropriate cell growth. The inhibition is intended to include inhibition of proliferation including rapid proliferation. The term "inhibiting cancer cell growth" is also intended to encompass inhibiting tumor growth which includes the prevention of the growth of a tumor in a subject or a reduction in the growth of a pre-existing tumor in a subject. The inhibition also can be the inhibition of the metastasis of a tumor from one site to another. A cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "modulate" includes downregulation and upregulation. The term "downregulate," "decrease," "reduce," "inhibit," and the like are all used herein generally to mean a decrease by a statistically significant amount. The term "upregulate," "increase," "enhance," and the like are all used herein generally to mean an increase by a statistically significant amount. For example, an increase or a decrease can be by at least about 10%, 20%, 25%, 30%, 35%, 40%, 45%, 50%, 55%, 60%, 65%, 70%, 75%, 80%, 85%, 90%, 95%, 98%, 99%, 100%, 150%, 200%, 250%, 300%, 350%, 400%, 450%, 500%, 1000%, or more or any range in between 10-1000% inclusive as compared to a control. In some embodiments, the control can be a change in a cancer cell state such as cancer cell proliferation in the presence versus the absence of treatment. In another embodiment, the control can be activity of a wild type polypeptide of interest. An "overactivity" or "significantly higher level of activity" refers to an activity level of a molecule or test sample that is greater than the standard error of the assay employed to assess the activity, and is preferably at least twice, and more preferably three, four, five or ten or more times the activity relative to a reference or control sample and preferably, the average activity in several control samples. The term "underactivity" refers to the opposite of "overactivity."

A cancer and/or tumor cell is "resistant" to a therapeutic agent if its rate of growth is not inhibited, or inhibited to a very low degree, as a result of contact with the therapeutic agent when compared to its growth in the absence of contact with the therapeutic agent. The quality of being resistant to a therapeutic agent is a highly variable one, with different cancer and/or tumor cells exhibiting different levels of "resistance" to a given therapeutic agent under different conditions.

A cancer and/or tumor cell is "sensitive" to a therapeutic agent if its rate of growth is inhibited as a result of contact with a therapeutic agent, compared to its growth in the absence of contact with the therapeutic agent. The quality of being sensitive to a therapeutic agent is a variable one, with different cancer and/or tumor cells exhibiting different levels of "sensitivity" to a given therapeutic agent, under different conditions.

Determination of whether a subject is "sensitive" or "resistant" to a therapeutic agent and/or protocol can be readily made by the physician (the "attending clinician"), as one skilled in the art, by the use of known techniques. For example, a number of factors are considered by the attending clinician, including, but not limited to: the specific cancer and/or tumor involved; pharmacodynamic characteristics of the particular therapeutic agent; the size, age, and general health of the patient; the degree of or involvement or the severity of the cancer and/or tumor; the particular compound administered; the mode of administration; and other relevant circumstances.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

As used herein, the term "synergistic" refers to a combination of therapeutic agents described herein, which, when taken together, is more effective than the additive effects of the individual therapies. A synergistic effect of a combination of therapies (e.g., a combination of therapeutic agents such as but not limited to a combination of a CNL and a tyrosine kinase inhibitor and/or a nuclear receptor inhibitor) permits the use of lower dosages of one or more of the therapeutic agent(s) and/or less frequent administration of the agent(s) to a subject with a disease or disorder, e.g., a proliferative disorder. The ability to utilize lower the dosage of one or more therapeutic agent and/or to administer the therapeutic agent less frequently reduces the toxicity associated with the administration of the agent to a subject without reducing the efficacy of the therapy in the treatment of a disease or disorder. In addition, a synergistic effect can result in improved efficacy of agents in the prevention, management, and/or treatment of a disease or disorder, e.g. a proliferative disorder such as but not limited to a cancer and/or a tumor. Finally, a synergistic effect of a combination of therapies may avoid or reduce adverse or unwanted side effects associated with the use of either therapeutic agent alone. As used herein, the term "in combination" refers to the use of more than one therapeutic agent. The use of the term "in combination" does not restrict the order in which the therapeutic agents are administered to a subject with a disease or disorder, e.g., a proliferative disorder. A first therapeutic agent, such as a CNL as described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as an anti-cancer and/or anti-tumor agent, in some embodiments a receptor tyrosine kinase inhibitor or a nuclear receptor inhibitor, to a subject with a disease or disorder, e.g. a proliferative disorder, such as a cancer and/or a tumor.

II. Ceramide NanoLiposomes

The use of ceramides such as but not limited to short chain ceramides such as $C_2$ and $C_6$ ceramides has drawn attention due to its success as a therapeutic agent in tumor models. The instant co-inventors have developed several NanoLiposome formulations that include, for example, $C_2$-$C_{24}$ ceramides, in some embodiments $C_6$ ceramides, which are referred to herein as Ceramide NanoLiposomes (CNLs; see U.S. Pat. Nos. 8,747,891; 9,028,863; 9,326,953; and 10,045,953, each of which is incorporated by reference in its entirety). CNLs provide highly specific delivery to cancer and tumor cells of ceramides and other cargo including but not limited to agents with anti-cancer and/or anti-tumor biological activities. Thus, disclosed herein are the results of employing CNLs as anti-tumor and anti-cancer agents in various in vitro models of cancer.

It is noted, however, that delivery vehicles other than nanoliposomes can deliver ceramides and in some embodiments additional therapeutic agents to cells. Other delivery vehicles including, but not limited to nanospheres, microspheres, resorbable and non-aggregating nanoparticle dispersions, metal or semiconductor nanoparticles, or polymeric materials such as dendrimers or hydrogels, each of which exhibit improved lipid solubility, cell permeability, an increased circulation half-life and pharmacokinetic profile with improved tumor or vascular targeting can be employed. Exemplary such delivery vehicles are known to those of skill in the art and are disclosed in, for example, U.S. Pat. No. 9,028,863.

Thus, suitable active agent carriers include, for example, liposomes, nanoparticles, micelles, microbubbles, and the like. Techniques for incorporating active agents into such carriers are known in the art. For example, liposomes or lipidic particles can be prepared in accordance with U.S. Pat. No. 5,077,057 to Szoka Jr. Liposomes formed from non-phosphal lipid components which have the potential to form lipid bilayers are disclosed in Brockerhoff & Ramsammy, 1982. For the preparation, purification, modification, and loading of liposomes, see generally New, 1990. A general discussion of techniques for preparation of liposomes and of medication encapsulating liposomes can be found in U.S. Pat. No. 4,224,179 to Schneider. See also Mayer et al., 1986. See also U.S. Pat. No. 6,083,539 to Yamada & Iljima for the encapsulation of an active agent dry powder composition. For incorporation of active agents into nanoparticles, see e.g., de Villiers et al., 2009. For incorporation of active agents into micelles, see e.g., Lu & Oie, 2004.

Nonetheless, in some embodiments the presently disclosed subject matter provides ceramide nanoliposomes (CNLs) encapsulating one or more anti-cancer and/or anti-tumor agents. In some embodiments, the ceramide nanoliposomes comprise a lipid bilayer comprising one or more ceramides, optionally one or more $C_2$-$C_{24}$ ceramides.

In some embodiments, the CNLs are employed alone, and in some embodiments the CNLs encapsulate one or more anti-cancer and/or anti-tumor agents. In some embodiments, the one or more anti-cancer and/or anti-tumor agents are selected from the group consisting of tyrosine kinase receptor inhibitors and nuclear receptor inhibitors.

As used herein, the term "tyrosine kinase inhibitor" (TKI) refers to a molecule or composition that inhibits a biological activity of a tyrosine kinase, in some embodiments a receptor tyrosine kinase, which in some embodiments is a receptor tyrosine kinase that is associated with a cancer and/or a tumor. Exemplary TKIs are compounds that inhibit one or more biological activities of an EGFR, referred to broadly as "EGFR inhibitors". EGFR inhibitors include, but are not limited to small molecules and antibodies, particularly monoclonal antibodies and paratope-containing fragments and derivatives thereof. Exemplary, non-limiting EGFR inhibitors include Afatinib (CAS No. 850140-72-6), Lapatinib (CAS No. 231277-92-2), Neratinib (CAS No. 698387-09-6), Gefitinib (CAS No.: 184475-35-2), Erlotinib (CAS No. 183321-74-6), Canertinib CAS No. 267243-28-7), Pelitinib (CAS No. 257933-82-7), Sapitinib (CAS No. 848942-61-0), Osimertinib (CAS No. 1421373-65-0), Varlitinib (CAS No. 845272-21-1), Icotinib (CAS No. 610798-31-7), and the various EGFR inhibitors available from Selleckchem (Houston, Texas, United States of America) including, but not limited to AG-490 (CAS No. 133550-30-8), CP-724,714 (CAS No. 383432-38-0), Dacomitinib (CAS No. 1110813-31-4), WZ4002 (CAS No. 1213269-23-8), CUDC-101 (CAS No. 1012054-59-9), AG-1478 (CAS No. 153436-

53-4), PD153035 (CAS No. 153436-54-5), AEE788 (CAS No. 497839-62-0), AC480/BMS-599626 (CAS No. 714971-09-2), AP26113-analog (ALK-IN-1; CAS No. 1197958-12-5), OSI-420 (CAS No. 183320-51-6), WZ-3146 (CAS No. 1214265-56-1), AST-1306 (CAS No. 897383-62-9), Rociletinib (CO-1686; AVL-301; CAS No. 1374640-70-6), TAK-285 (CAS No. 871026-44-7), WHI-P154 (CAS No. 211555-04-3), Daphnetin (7,8-dihydroxycoumarin), PD168393 (CAS No. 194423-15-9), CNX-2006 (CAS No. 1375465-09-0), Tyrphostin 9 (CAS No. 10537-47-0), AG 18 (CAS No. 118409-57-7), Avitinib (AC0010; CAS No. 1557268-88-8), Lazertinib (YH25448; GNS-1480; CAS No. 1903008-80-9), Lifirafenib (BGB-283; CAS No. 1446090-77-2), Nazartinib (EGF816; NVS-816; CAS No. 1508250-71-2), Brigatinib (AP26113; CAS No. 1197953-54-0), AZD3759 (CAS No. 1626387-80-1), CL-387785 (EKI-785; CAS No. 194423-06-8), Poziotinib (HM781-36B; CAS No. 1092364-38-9), HER2-Inhibitor-1 (CAS No. 937265-83-3), WZ8040 (CAS No. 1214265-57-2), Genistein (CAS No. 446-72-0), Naquotinib (ASP8273; CAS No. 1448232-80-1), Olmutinib (HM61713; BI 1482694; CAS No. 1353550-13-6), Butein (CAS No. 487-52-5), and analogs and pharmaceutically acceptable salts thereof. Other exemplary, non-limiting EGFR inhibitors include anti-EGFR antibodies, including but not limited to trastuzumab (sold under the brand name HERCEPTIN® by Genentech, Inc., South San Francisco, California, United States of America), cetuximab (sold under the trade name ERBITUX® by Bristol-Myers Squibb, New York City, New York, United States of America), panitumumab (also called ABX-EGF; sold under the trade name VECTIBIX® by Amgen Inc., Thousand Oaks, California, United States of America), pertuzumab (sold under the trade name PERJETA® by Genentech, Inc., South San Francisco, California, United States of America), and matuzumab (also called EMD 72000; see U.S. Pat. No. 5,558,864), as well as paratope-containing fragments and derivatives of these anti-EGFR antibodies.

As used herein, the term "nuclear receptor inhibitor" (NRI) refers to a molecule or composition that inhibits a biological activity of a nuclear receptor, which in some embodiments is an androgen receptor or an estrogen receptor. Exemplary NRIs include abiraterone acetate, enzalutamide, tamoxifen, raloxifene, and toremifene, as well as analogues and pharmaceutically acceptable salts thereof. In some embodiments, the nuclear receptor inhibitor is an inhibitor of a cytochrome P450 family 17 subfamily A member 1 (CYP17A1) biological activity and/or is an AR antagonist. Abiraterone acetate and enzalutamide are exemplary CYP17A1 antagonists In some embodiments, the CNLs of the presently disclosed subject matter are provided as pharmaceutical compositions comprising a CNL as disclosed herein and one or more pharmaceutically acceptable carriers or diluents. In some embodiments, the pharmaceutical composition is pharmaceutically acceptable for use in a human.

Thus, in some embodiments the CNLs of the presently disclosed subject matter can in some embodiments further comprise one or more pharmaceutically acceptable carriers or diluents. In some embodiments, a ceramide nanoliposome (CNL) of the presently disclosed subject matter comprises a pharmaceutical composition that includes a pharmaceutically acceptable carrier. Suitable formulations include aqueous and non-aqueous sterile injection solutions that can contain anti-oxidants, buffers, bacteriostats, bactericidal antibiotics, and solutes that render the formulation isotonic with the bodily fluids of the subject; and aqueous and non-aqueous sterile suspensions, which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in some embodiments in the range of 0.1 to 10 mg/ml, in some embodiments about 2.0 mg/ml; and/or mannitol or another sugar, in some embodiments in the range of 10 to 100 mg/ml, in some embodiments about 30 mg/ml; and/or phosphate-buffered saline (PBS). Any other agents conventional in the art having regard to the type of formulation in question can be used.

The methods and compositions of the presently disclosed subject matter can also be employed in combination with a potentiator. A "potentiator" can be any material that improves or increases the efficacy of a pharmaceutical composition and/or acts on the immune system. Exemplary potentiators are triprolidine and its cis-isomer, which can be used in combination with chemotherapeutic agents. Triprolidine is described in U.S. Pat. No. 5,114,951. Other potentiators are procodazole 1H-Benzimidazole-2-propanoic acid; [β-(2-benzimidazole) propionic acid; 2-(2-carboxyethyl)benzimidazole; propazol). Procodazole is a non-specific active immunoprotective agent against viral and bacterial infections and can be used with the compositions disclosed herein. Potentiators can improve the efficacy of the disclosed compositions and can be used in a safe and effective amount.

The CNLs of the presently disclosed subject matter can in some embodiments be administered parenterally, systemically, and/or topically. By way of example and not limitation, composition injection can be performed by intravenous (i.v.) injection, sub-cutaneous (s.c.) injection, intradermal (i.d.) injection, intraperitoneal (i.p.) injection, and/or intramuscular (i.m.) injection. One or more such routes can be employed. Parenteral administration can be, for example, by bolus injection or by gradual perfusion over time. Alternatively or concurrently, administration can be by the oral route. In some embodiments, a CNL of the presently disclosed subject matter is administered intratumorally, such as by depot. In some embodiments, intradermal (i.d). injection is employed. The CNLs of the presently disclosed subject matter are suitable for administration by any acceptable route such as oral (enteral), nasal, ophthal, or transdermal. In some embodiments, the administration is subcutaneous and can be administered by an infusion pump.

III. Methods of Using the CNLs of the Presently Disclosed Subject Matter

The CNLs of the presently disclosed subject matter can be employed for modulating undesirable growth and/or proliferation of cells in whatever context. In some embodiments, the CNLs of the presently disclosed subject matter are employed to inhibit the growth and/or proliferation of cancer and/or tumor cells.

Thus, in some embodiments, the CNLs of the presently disclosed subject matter are employed in a method for treating a cancer and/or a tumor in a subject, the method comprising administering to the subject an effective amount of a ceramide nanoliposome (CNL), wherein the CNL comprises a lipid bilayer comprising one or more $C_2$-$C_{24}$ ceramides and encapsulates one or more anti-cancer and/or anti-tumor agents.

In some embodiments, the CNLs of the presently disclosed subject matter are employed in a method for treating a cancer and/or a tumor associated with activity of a receptor tyrosine kinase or a nuclear receptor in a subject, the method comprising administering to the subject an effective amount of a ceramide nanoliposome (CNL), wherein the CNL comprises a lipid bilayer comprising one or more $C_2$-$C_{24}$ ceramides and encapsulates one or more nuclear receptor inhibitors, one or more tyrosine kinase inhibitors, or a combination thereof.

In some embodiments, the CNLs of the presently disclosed subject matter are employed in a method for treating Prostate Cancer (PCa) in a subject, the method comprising administering to the subject an effective amount of a ceramide nanoliposome (CNL), wherein the CNL comprises a lipid bilayer comprising one or more $C_2$-$C_{24}$ ceramides and encapsulates one or more anti-cancer and/or anti-tumor agents.

In some embodiments, the CNLs of the presently disclosed subject matter are employed in a method for inhibiting growth of an EGFR-dependent cancer and/or tumor, the method comprising contacting the EGFR-dependent cancer or tumor with an effective amount of a ceramide nanoliposome (CNL), wherein the CNL comprises a lipid bilayer comprising one or more $C_2$-$C_{24}$ ceramides and encapsulates one or more anti-cancer and/or anti-tumor agents.

As disclosed herein the CNLs of the presently disclosed subject matter are capable of inducing apoptosis or otherwise inhibiting the growth of androgen receptor (AR) negative cells. Thus, in some embodiments the CNLs of the presently disclosed subject matter method are employed in a method for inhibiting growth of an androgen receptor (AR) negative cell, optionally an AR negative cell in a subject. In some embodiments, the presently disclosed method comprises contacting the AR negative cell with an effective amount of a ceramide to nanoliposome (CNL), wherein the CNL comprises a lipid bilayer comprising one or more $C_2$-$C_{24}$ ceramides and encapsulates one or more anti-cancer and/or anti-tumor agents.

In some embodiments, the AR negative cells are present in the prostate of a subject. As such, the CNLs of the presently disclosed subject matter are in some embodiments employed in a method of reducing or eliminating AR negative cells from a subject's prostate by administering to the subject an effective amount of a ceramide nanoliposome (CNL) comprising a lipid bilayer comprising one or more $C_2$-$C_{24}$ ceramides and encapsulating one or more anti-cancer and/or anti-tumor agents, wherein the CNL contacts the AR negative cells and induces apoptosis thereof.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods for the EXAMPLES

Cell culture. Human PCa cell lines were kindly provided by the Gioeli lab at the University of Virginia, Charlottesville, Virginia, United States of America (LNCaP, 22Rv1, C4-2, VCaP, DU145 and PC-3); the Voelkel-Johnson lab at the Medical University of South Carolina, Charleston, South Carolina, United States of America (PPC-1). The Paschal lab at the University of Virginia kindly provided the non-malignant prostate cell line RWPE-1. LNCaP and C4-2 were cultured using DMEM/F 12 medium (Gibco Laboratories, Gaithersburg, Maryland, United States of America) supplemented with 5% Fetal Bovine Serum (FBS, Gemini Bio Products) 1% antibiotic/antimycotic (Gibco), and 1% Insulin-Transferrin Selenium (ITS, Corning). VCaP, 22Rv1, PC-3 were culture in DMEM (Gibco) supplemented with 5% Heat-inactivated FBS and 1% of antibiotic/antimicotic. DU145, PPC-1 were cultured in RPMI1840 (Gibco) supplemented with 10% FBS and 1% antibiotic/antimicotic. RWPE-1 cells were cultured in Keratinocyte-FSM medium (Gibco) supplemented according to manufacturer instructions and 1% antibiotic/antimicotic. Human HNSCC cell lines were kindly provided by the Jameson lab at the University of Virginia (Cal-27, FaDu, UNC-7, UNC-10, SCC-9, SCC-25, SCC-61, & OSC-19). All cell lines were cultured using DMEM/F12 medium (Gibco) supplemented with 10% FBS and 1% antibiotic/antimycotic (Gibco). The SCC-9 & SCC-61 cells line were additionally supplemented with 1 μg/mL hydrocortisone (Sigma-Aldrich, St. Louis, Missouri, United States of America). All cell lines were cultured using a recommended medium supplemented with 1% of Antibiotic-Antimycotic and maintained at 37° C. and 5% $CO_2$ in a humidified chamber.

Drugs concentrations. Experiments for determining CNL $IC_{50}$ values used a range of increased concentrations: 1 μM, 5 μM, 10 μM, 20 μM, 50 μM. For synergistic experiments: abiraterone acetate (Selleckchem, Houston, Texas, United States of America) was used at 0.5 μM, 1 μM, 5 μM, 10 μM, 20 μM; enzalutamide (Selleckchem) at 1 μM, 5 μM, 10 μM, 20 μM, 30 μM; and CNL at 5 μM, 10 μM, 20 μM, and 30 μM. During synergy studies, each concentration of either abiraterone acetate or enzalutamide was combined with either Ghost (negative) control (nanoliposomes without the $C_6$ ceramide—active agent) or each concentration of CNL. Respective negative controls for abiraterone acetate and enzalutamide were also used. Synergy experiments were performed in LNCaP and C4-2 cells. For synergistic studies using the HNSCC cell lines, all eight cell lines were pretreated for one hour with either Erlotinib (Selleckchem) or Gefitinib (Sigma-Aldrich Corporation, St. Louis, Missouri, United States of America) before adding CNL. Six different concentrations of Erlotinib and Gefitinib (0 μM, 0.5 μM, 1 μM, 5 μM, 10 μM, and 25 μM) were tested against five different CNL concentrations (0 μM, 2.5 μM, 5 μM, 10 μM, and 25 μM). Both Erlotinib and Gefitinib were first dissolved in dimethyl sulfoxide (DMSO) and all future dilutions were in water. CNL initial dilution was into phosphate-buffered saline (1× PBS at pH 7.4; Gibco) as were future dilutions. Equivalent amounts of negative controls (DMSO for Gefitinib & Erlotinib/Ghost Liposomes for CNL) were used in all dilutions to ensure uniformity in treatments.

Cell viability assays. To evaluate cell viability in prostate cell lines after drug exposure, prostate cells were plated in 96-well plates. After 24 hours, cells were exposed to each drug alone or in combination, and viability was measured every 24 hours for a total of 72 hours. Viability was assayed using a CELLTITER 96® brand AQueous Non-Radioactive Cell Proliferation MTS Assay (Promega Corporation, Madison, Wisconsin, United States of America) according to the manufacturer's instructions. Three biologically independent experiments were performed. Results were normalized to the respective negative controls of each experiment. Cells were plated to have a 50-60% confluence by the time drugs were added to the media. PC-3, DU145, and PPC-1 were seeded at $5 \times 10^4$ cells per mL; VCaP, 22Rv1, LNCaP, and C4-2 plated at 1×10⁵ cells per mL; RWPE-1 plated at 2×10⁵ cells per mL. In 96-well plates, 100 µL of cells were used per well.

To evaluate cell viability in HNSCC cell lines after drug exposure, 5,000 cells were plated in 96-well plates. After 16-30 hours, cells were exposed to each drug alone or in combination, and viability was measured every 24 hours for a total of 48 hours. Viability was assayed using a CELLTITER 96® brand AQueous Non-Radioactive Cell Proliferation MTS Assay (Promega Corporation) according to manufacturer's instructions. A minimum of three biologically independent experiments were performed. Results were normalized to the respective negative controls of each experiment.

Cell death assays. In order to evaluate cell death in prostate cell lines exposed to CNL and/or abiraterone acetate or enzalutamide, a flow cytometry assay was performed. Cells were plated in 96-well plates for 24 hours before being exposed to the drug concentrations mentioned above. After 72 hours, cells were stained with a Fixable Viability Dye EFLUOR™ 780 brand a viability dye (ThermoFischer Scientific Inc., Waltham, Massachusetts, United States of America) according to the manufacturer's recommendations. The use of this dye facilitated differentiation between two cell populations: dead or live cells. Flow cytometry controls (alive/stained; alive/non-stained; dead/stained; dead/non-stained) were used to allow for a more rigorous discrimination between populations. Results were normalized to the respective negative controls of each experiment. Data analysis was performed using FlowJo Software.

To evaluate cell death in HNSCC cell lines exposed to CNL and/or Erlotinib or Gefitinib, a flow cytometry assay was performed. Cells were plated in 24-well plates for 16-30 hours before being pre-treated for one hour with Erlotinib or Gefitinib (0 µM, 10 µM, 25 µM) and then with CNL (0 µM, 2.5 µM, 5 µM). After 24 or 48 hours, cells were stained with a Fixable Viability Dye EFLUOR™ 780 brand a viability dye (ThermoFischer Scientific Inc.)

according to the manufacturer's recommendations. The use of this dye allowed us to differentiate between two cell populations: dead or live cells. Flow cytometry controls (alive/stained, alive/non-stained, & dead/stained) were used to allow for a more rigorous discrimination between populations. Results were normalized to the respective negative controls of each experiment. Data analysis was performed using FlowJo Software.

Example 1

Preparation of NanoLiposome Formulations Comprising Ceramides (CNLs)

CNLs were prepared essentially as described in U.S. Pat. No. 9,028,863 (incorporated herein by reference in its entirety). Briefly, lipids, dissolved in chloroform ($CHCl_3$), were combined in specific molar ratios, dried under a stream of nitrogen above lipid transition temperatures, and hydrated with sterile phosphate-buffered saline (PBS). The resulting solution underwent sonication for 2 minutes followed by extrusion through 100 nm polycarbonate membranes. Incorporation efficiency was determined by incorporating trace amounts of $[^3H]C_6$ in the formulation, extracting constituent lipids in $CHCl_3$/MeOH (2:1), and comparing radioactivity before and after extrusion using a scintillation counter. Formulations for in vivo administration were comprised of DSPC:DOPE:DSPE-PEG(5000):$C_8$-Ceramide-PEG(750):$C_6$-Ceramide (3.75:1.75:0.75:0.75:3.0, molar ratios). The addition of PEG(750)-$C_8$ allows for up to 40 molar percent $C_6$-ceramide. The bioactivity of these pegylated formulations were confirmed in 410.4 mammary adenocarcinoma cells. The composition of formulated liposomes was validated by extracting constituent lipids in chloroform/methanol (2:1), followed by resolution on preheated silica gel 60 thin layer chromatography (TLC) plates using a $CHCl_3$/MeOH/ddH2O (60:25:4) solvent system. Lipids were visualized in an iodine chamber. Transmission electron microscopy (TEM) was utilized to characterize the size and morphology of the formulated liposomes.

Example 2

CNL Were More Efficacious in AR Negative PCa Cells

To evaluate cell viability in prostate cell lines after drug exposure, prostate cells were plated in 96-well plates. Cells were plated to have a 50-60% confluence by the time drugs were added to the media. PC-3, DU145, and PPC-1 were seeded at 5×10⁴ cells per mL; VCaP, 22Rv1, LNCaP, and C4-2 plated at 1×10⁵ cells per mL; RWPE-1 plated at 2×10⁵ cells per mL. In 96-well plates, 100 µL of cells were used per well. After 24 hours, cells were exposed to CNLs at 1 µM, 5 µM, 10 µM, 20 µM, and 50 µM, and viability was measured every 24 hours for a total of 72 hours. Viability was assayed using an MTS assay (CELLTITER 96® AQueous Non-Radioactive Cell Proliferation Assay, Promega Corporation, Madison, Wisconsin, United States of America) according to manufacturer's instructions. Three biologically independent experiments were performed. Results were normalized to the respective negative controls of each experiment and are shown in FIG. 1 and in Table 1.

TABLE 1

Summary of Cell Lines Employed, AR Statuses, and $IC_{50}$ Values at 48 Hours Post-treatment

| Cell Line | AR Status | $IC_{50}$ at 48 Hours |
|---|---|---|
| PC-3 | Negative | 8.5 µM |
| PPC-1 | Negative | 10 µM |
| DU145 | Negative | 11.4 µM |
| VCaP | Positive | 25 µM |
| Rv1 | Positive | 30 µM |
| C4-2 | Positive | 31 µM |
| LNCaP | Positive | 37 µM |
| RWPE-1* | Positive | >50 µM |

*RWEPE-1 is a normal prostate cell line

It was observed that PCa cell lines that lacked the androgen receptor (AR) were more sensitive to CNL treatment than AR positive cells. It was determined that the $IC_{50}$ values at 48 hours for AR positive cells were at least two times higher than the $IC_{50}$ values at 48 hours for AR negative cells. This is important because AR negative cells, albeit rare, are cells that play an important for metastasis and tumor regrowth after hormonal treatment and that currently have no target therapies or even effective treatments.

Example 3

CNL Increased Cell Death in AR Negative PCa Cells

In order to evaluate cell death in prostate cell lines exposed to CNL, a flow cytometry assay was performed.

Cells were plated in 96-well plates for 24 hours before being exposed to CNLs at 5 µM, 10 µM, or 20 µM. After 24 hours, 48 hours, and 72 hours, cells were stained with a viability dye (Fixable Viability Dye EFLUOR™ 780, ThermoFischer Scientific) and Annexin V (Annexin V Apoptosis Detection Kit APC, ThermoFischer Scientific) according to the manufacturer recommendations. The use of this dye allowed for the differentiation of dead versus live cells. Flow cytometry controls (alive/stained; alive/non-stained; dead/stained; dead/non-stained) were used to allow for a more rigorous discrimination between populations. Results were normalized to the respective negative controls of each experiment. Data analysis was performed using FlowJo Software.

Figure 2A:
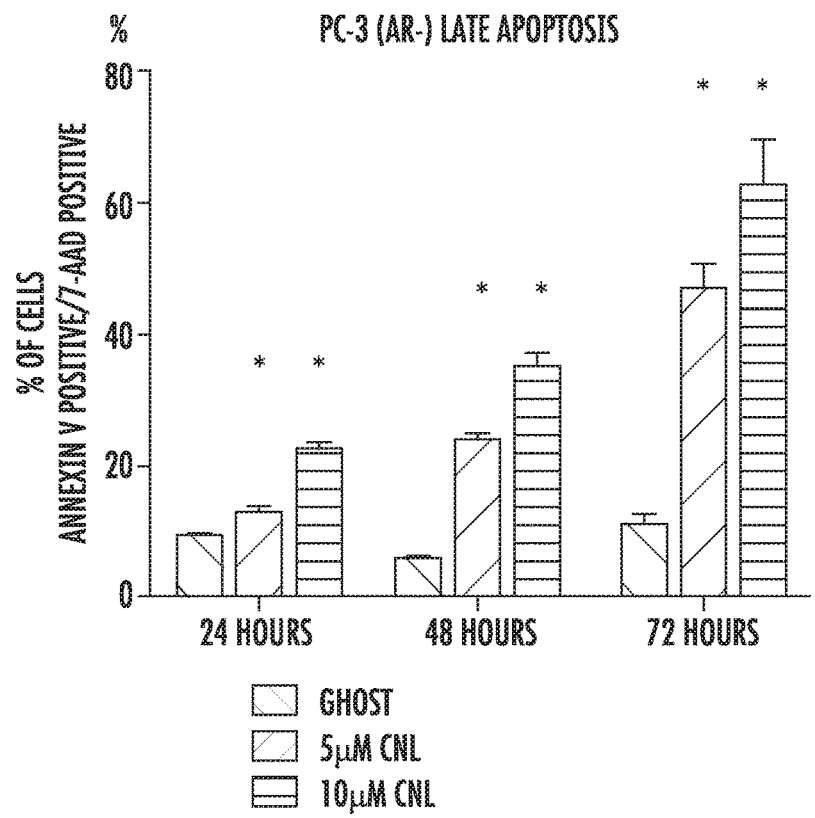
FIGS. 2A and 2B are a series of bar graphs showing the percentages of cells that were annexin V-positive and 7-aad-positive as an indicator of late apoptosis 24, 48, and 72 hours after treatment with various concentrations of CNL.
Figure 2B:
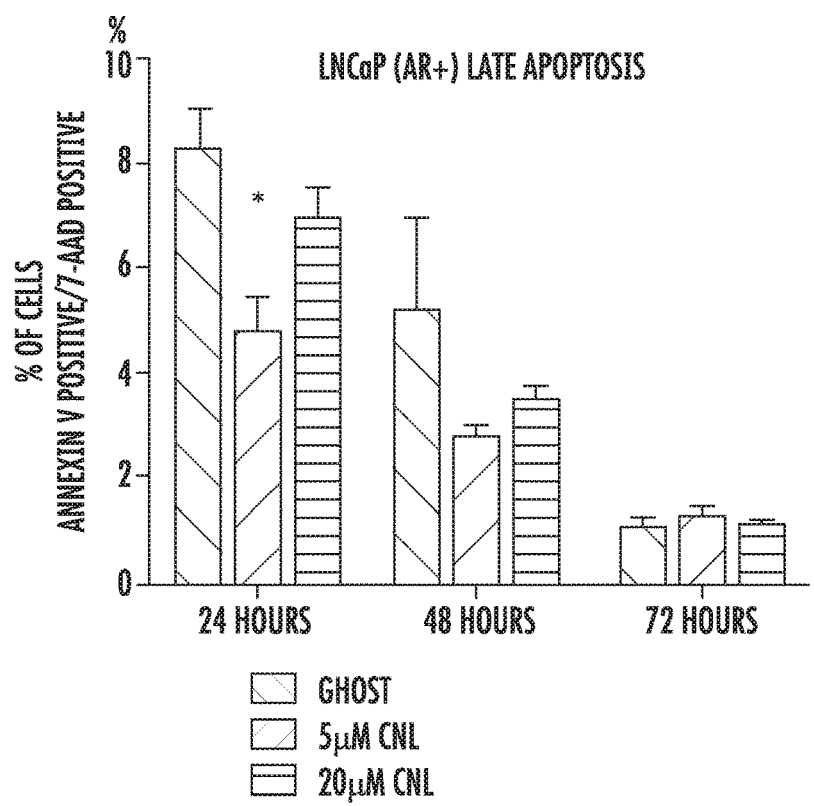

The results are presented in FIGS. 2A and 2B. As shown in FIGS. 2A and 2B, the results described in EXAMPLE 2 were validated using a flow cytometry assay by staining cells with 7-AAD (live/dead) and Annexin V (apoptosis). A double positive cell is considered dead and in late apoptosis stage. Again, treating PCa cells with CNLs generally resulted in cell death for the AR negative cells compared with AR positive counterparts.

Example 4

Pharmacological Blocking of AR Combined with CNL

To evaluate cell viability in prostate cell lines after drug exposure, prostate cells were plated in 96-well plates. Cells were plated to have a 50-60% confluence by the time drugs were added to the media. LNCaP and C4-2 cells were plated at $1\times10^5$ cells per mL and 100 µL were used per well. After 24 hours, cells were exposed to CNL at 5 µM, 10 µM, 20 µM, and 30 µM; Abiraterone Acetate (Selleckchem) at 0.5 µM, 1 µM, 5 µM, 10 µM, and 20 µM; Enzalutamide (Selleckchem) at 1 µM, 5 µM, 10 µM, 20 µM, and 30 µM; or combinations thereof. During synergy studies, each concentration of either Abiraterone Acetate or Enzalutamide was combined with either Ghost control (nanoliposomes without the $C_6$ ceramide—active agent) or each concentration of CNL. Respective negative controls for Abiraterone Acetate and Enzalutamide were used. Cell viability was measured every 24 hours for a total of 72 hours. Viability was assayed using MTS assay (Promega CELLTITER 96® AQueous Non-Radioactive Cell Proliferation Assay) according to manufacturer instructions. Three biologically independent experiments were performed. Results were normalized to the respective negative controls of each experiment.

Figure 3A:
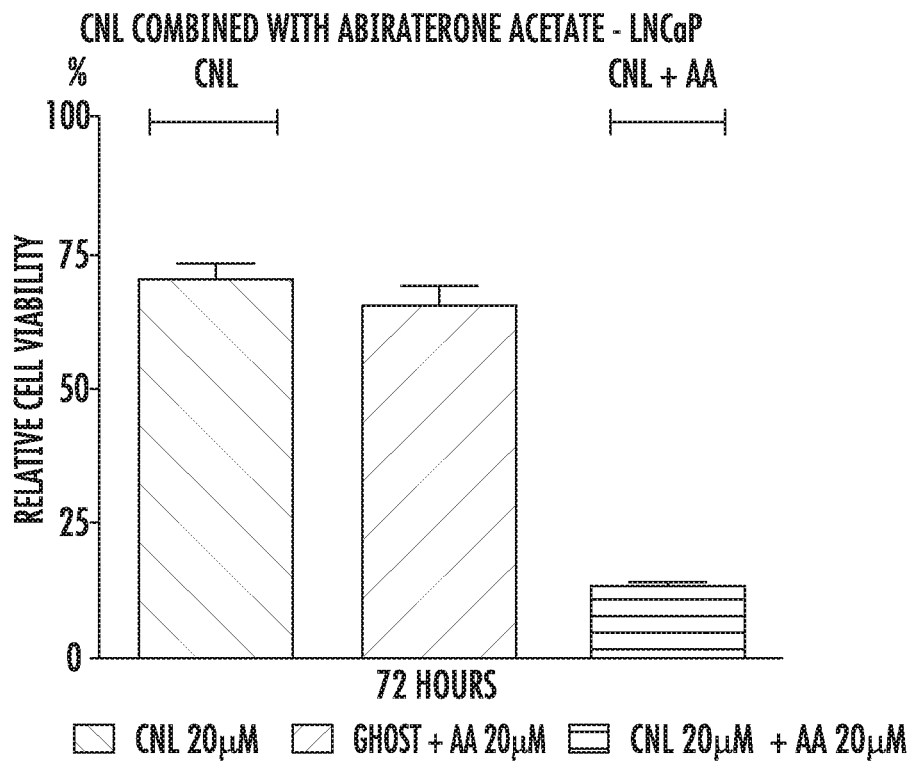
FIGS. 3A and 3B are a series of bar graphs showing that combination treatment with CNL combined with abiraterone acetate (FIG. 3A) or enzalutamide (FIG. 3B) had a synergistic effect in reducing cell viability in AR positive LNCaP cells as measured by MTS assay. The leftmost bars in FIGS. 3A and 3B show viabilities of LNCaP cells after 72 hours of treatment with 20 µM CNL alone. The middle bars in FIGS. 3A and 3B show viabilities of LNCaP cells after 72 hours of treatment with 20 µM abiraterone acetate (FIG. 3A) or 30 µM enzalutamide (FIG. 3B) alone. The rightmost bars in FIGS. 3A and 3B show viabilities of LNCaP cells after 72 hours of treatment with 20 µM CNL+20 µM abiraterone acetate (FIG. 3A) or 20 µM CNL+30 µM enzalutamide (FIG. 3B). The error bars correspond to one (1) standard deviation.
Figure 3B:
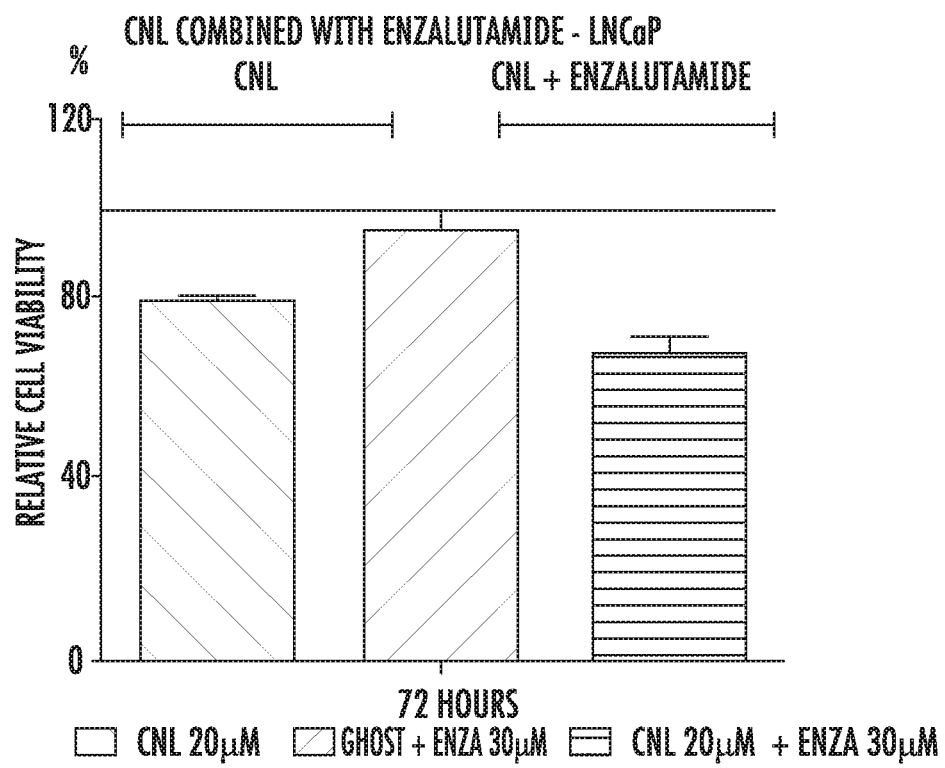

The results are presented in FIGS. 3A and 3B. As shown in FIGS. 3A and 3B, blocking hormonal synthesis with Abiraterone Acetate and/or antagonizing the androgen receptor with Enzalutamide combined with CNL resulted in a synergistic reduction in cell viability of AR positive cells, showing how promising this combination might be for PCa patients.

In order to validate the results shown in FIGS. 3A and 3B, a flow cytometry assay was performed. Cells were plated in 96-well plates for 24 hours before being exposed to the drug concentrations mentioned above. After 72 hours, cells were stained with a viability dye (Fixable Viability Dye EFLUOR™ 780, ThermoFischer Scientific) according to the manufacturer recommendations. The use of this dye allowed us to differentiate between two cell populations: dead or live cells. Flow cytometry controls (alive/stained; alive/non-stained; dead/stained; dead/non-stained) were used to allow for a more rigorous discrimination between populations. Results were normalized to the respective negative controls of each experiment. Data analysis was performed using FlowJo Software.

Figure 4A:
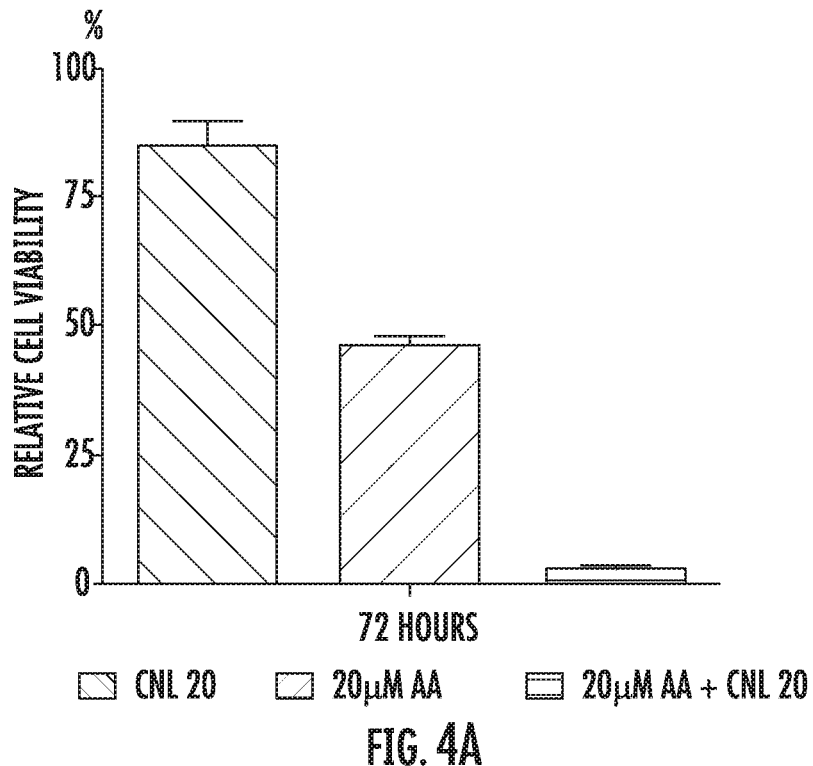
FIGS. 4A and 4B are a series of bar graphs showing that combination treatment with CNL combined with abiraterone acetate (AA.
Figure 4B:
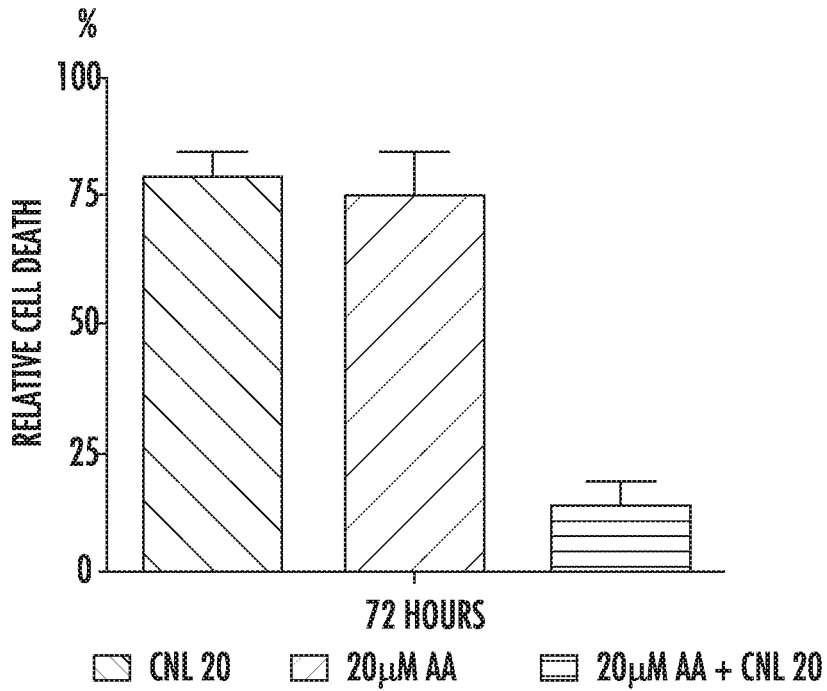

The results are presented in FIGS. 4A and 4B. As shown therein, combining CNL treatment with blocking hormonal synthesis with Abiraterone Acetate and/or antagonizing the androgen receptor with Enzalutamide resulted in a synergistic increase in cell death of AR positive cells, showing how promising this combination might be for PCa patients.

Figure 5A:
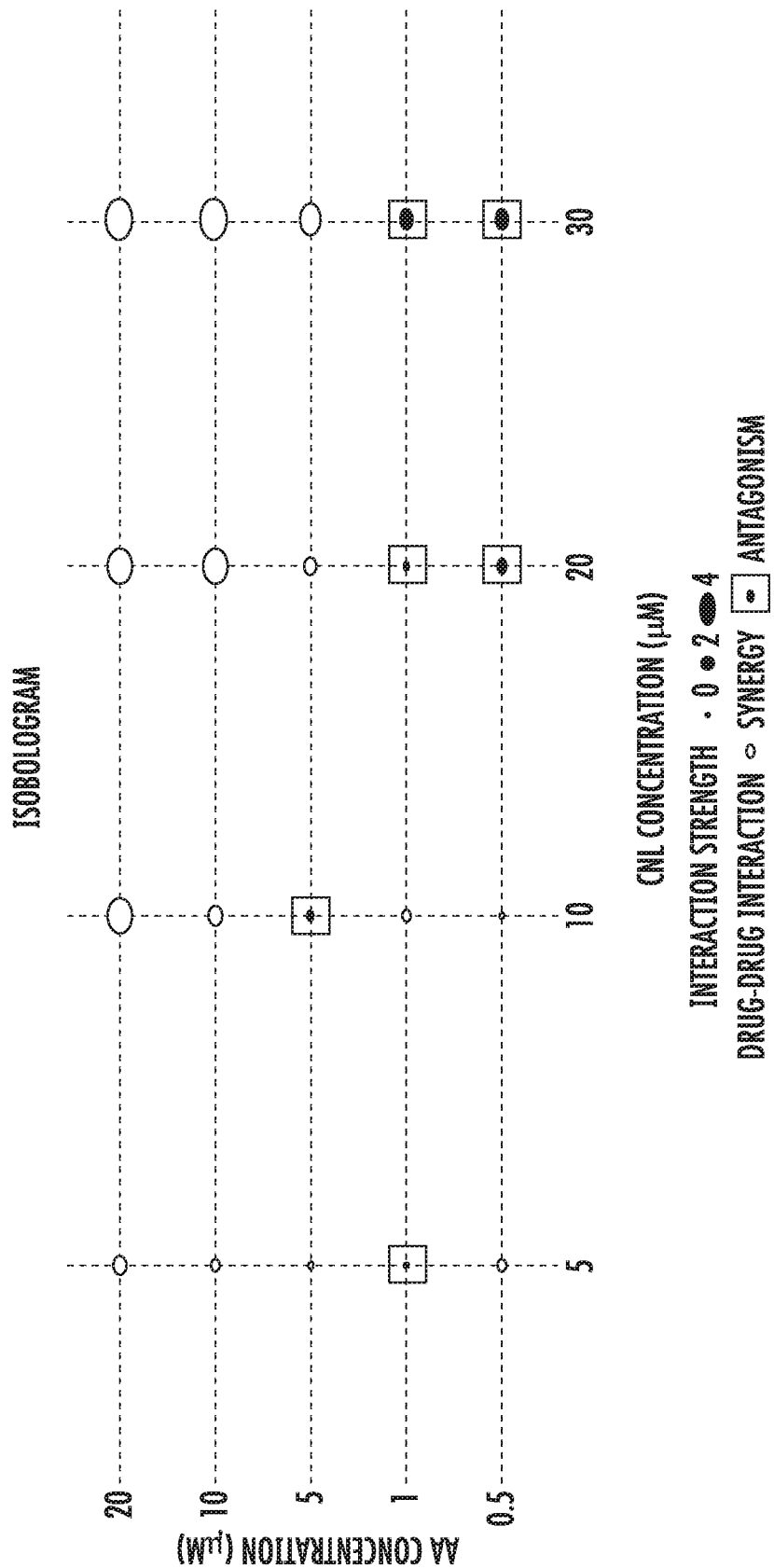
FIGS. 5A and 5B are a isobolograms showing degrees of synergy and antagonism between abiraterone acetate (AA.
Figure 5B:
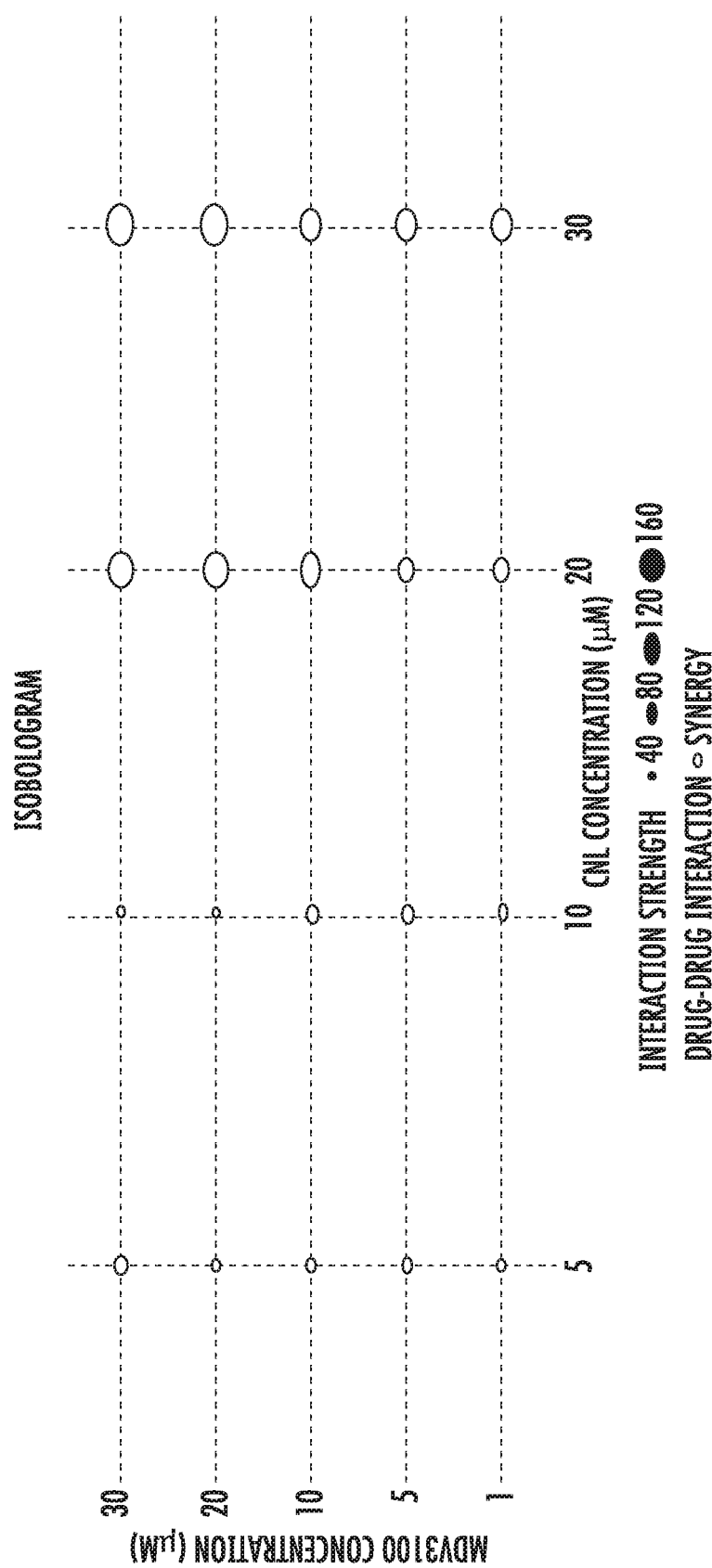

The synergy observed was quantified using an available online platform that is based on an application entitled "The Evaluation of Drug-Drug Combination Therapy Effect" available from the website https://xtmgah.shinyapps.io/DDCV/. Synergy was calculated based on the cell viability assay results and the isobolograms for the combinations of treatments are shown in FIGS. 5A and 5B. As shown in FIG. 5A, the degrees of synergism differed at various concentrations of Abiraterone Acetate and CNL, and in some cases actually the combination acted antagonistically. However, strong synergism was observed in several instances. With respect to FIG. 5B, strong synergism was shown with Enzalutamide and CNL at most concentration.

In order to evaluate lipid levels of prostate cell lines exposed to CNL and/or Abiraterone Acetate, a LC-MS/MS assay was performed. Cells were plated in 6-well plates for 48 hours before being exposed to CNL 10 µM and/or Abiraterone Acetate 10 µM, as well as respective controls (Ghost liposome and Ethanol respectively). Cells were collected after 1 hour, 4 hours, 12 hours, 24 hours, and 48 hours of exposure. Cells were lysed with 0.1× PBS and protein quantification was determined using a DC™ brand Protein Assay (Bio-Rad Laboratories, Inc., Hercules, California, United States of America). The Metabolomics core at University of Virginia performed lipid extraction, LC-MS/MS injections, and data analysis.

Figure 6A:
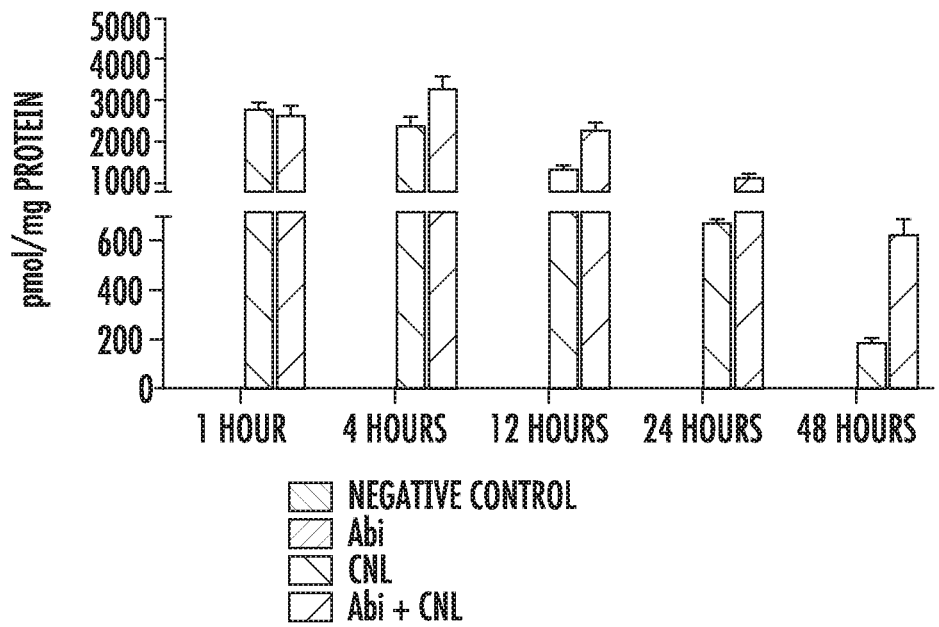
FIGS. 6A and 6B are a series of bar graphs presenting the results of experiments showing that AR signaling blockers led to a slower metabolism of CNLs and resulted in lipid accumulation in LNCaP cells as assayed by LC-MS/MS.
Figure 6B:
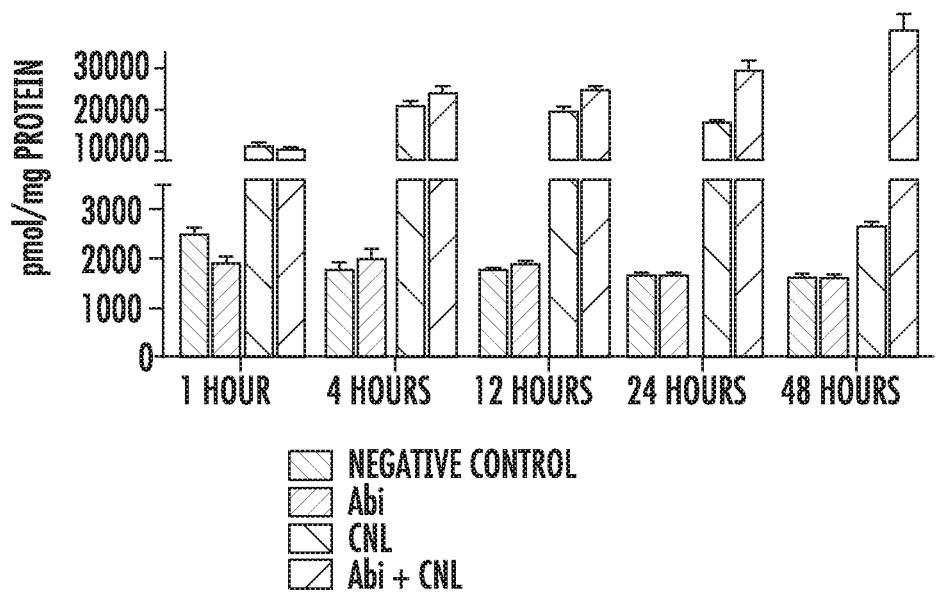

As shown in FIGS. 6A and 6B, when AR was blocked by abiraterone acetate, $C_6$ ceramide (FIG. 6A) and total ceramide levels (FIG. 6B) were not changed. However, when combined with CNL, metabolism and conversion of $C_6$-ceramide to endogenous/natural ceramides was slowed down, and accumulation of total levels of ceramide was increased, which results in cell death.

Example 5

Erlotinib Alone was Minimally Effective at Killing HNSCC

To evaluate cell viability of HNSCC cell lines after exposure to various amounts of Erlotinib, 5,000 UNC-10 or SCC-25 cells were plated in 96-well plates. After 16-30 hours, cells were exposed to each Erlotinib at 0 µM, 0.5 µM, 1 µM, 5 µM, 10 µM, and 25 µM, and viability was measured at 24 and 48 hours. Viability was assayed using MTS assay (Promega CELLTITER 96® AQueous Non-Radioactive Cell Proliferation Assay) according to manufacturer instructions. A minimum of three biologically independent experiments were performed. Results were normalized to the respective negative controls of each experiment.

Figure 7A:
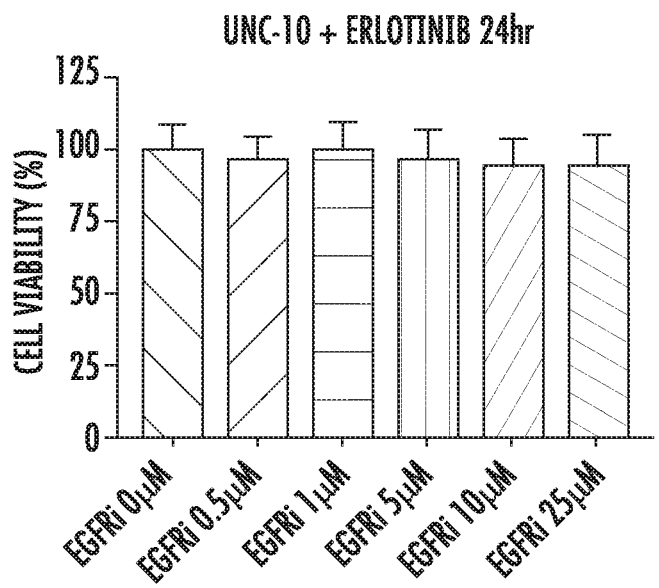
FIGS. 7A-7D are a series of bar graphs showing the results of cell viability as measured by MTS assays of HNSCC cells exposed to various concentrations of the EGFR inhibitor (EGFRi) for 24 or 48 hours.
Figure 7B:
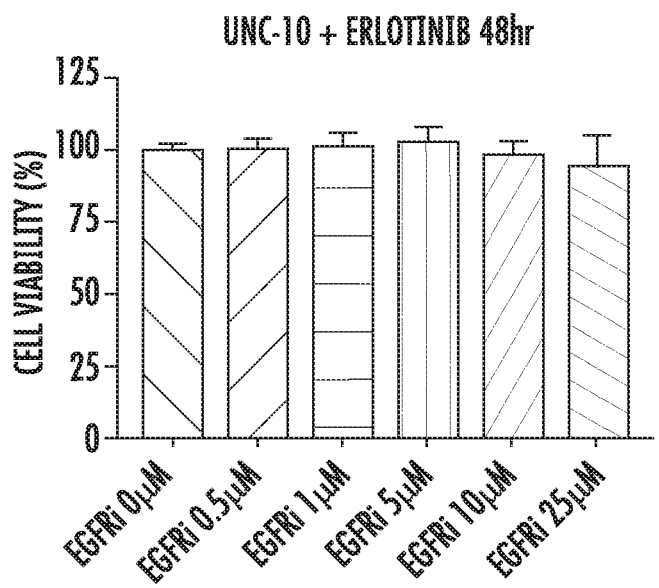
Figure 7C:
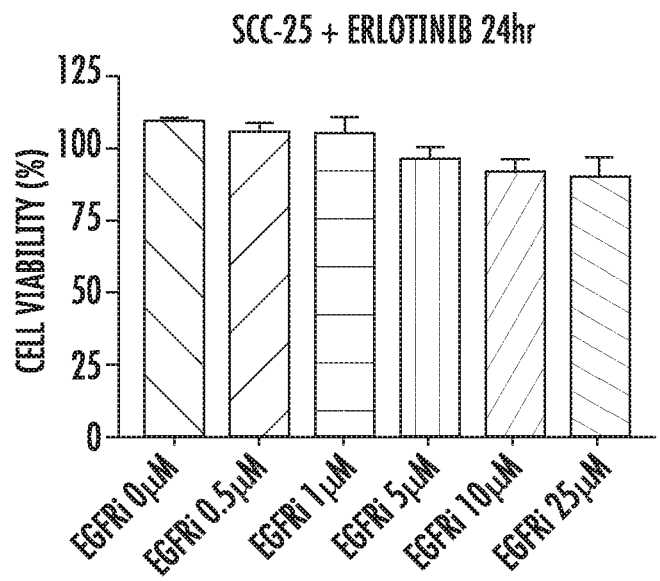
Figure 7D:
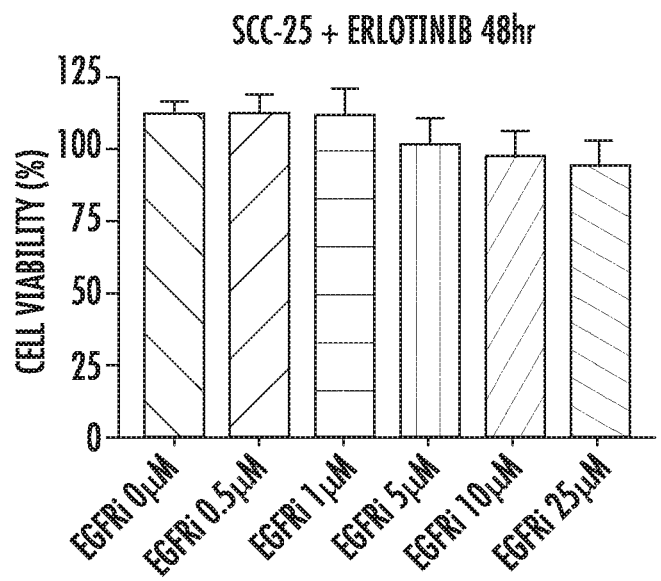

As shown in FIGS. 7A and 7B, Erlotinib (EGFRi) alone had little effect on UNC-10 cell viability at 24 or 48 hours. There was some effect on SCC-25 cells at higher concentrations, but the effect was not statistically significant (see FIGS. 7C and 7D).

Example 6

Gefitinib was Minimally Effective at Killing HNSCC

Figure 8A:
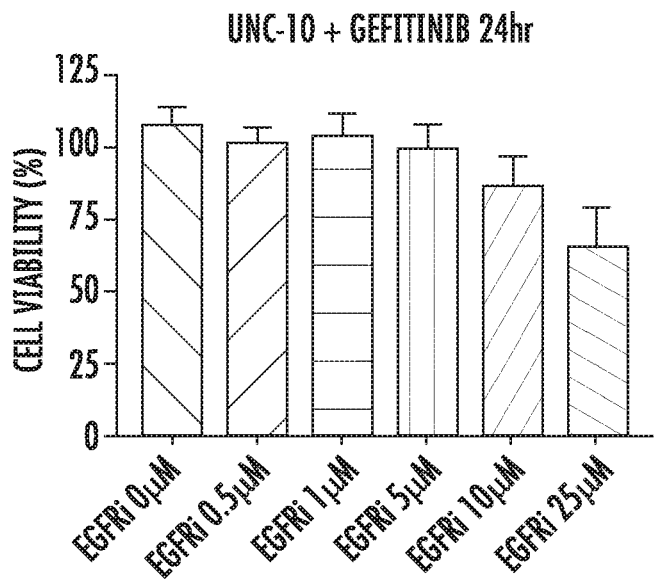
FIGS. 8A-8D are a series of bar graphs showing the results of cell viability as measured by MTS assays of HNSCC cells exposed to various concentrations of the EGFR inhibitor (EGFRi) Gefitinib for 24 or 48 hours.
Figure 8B:
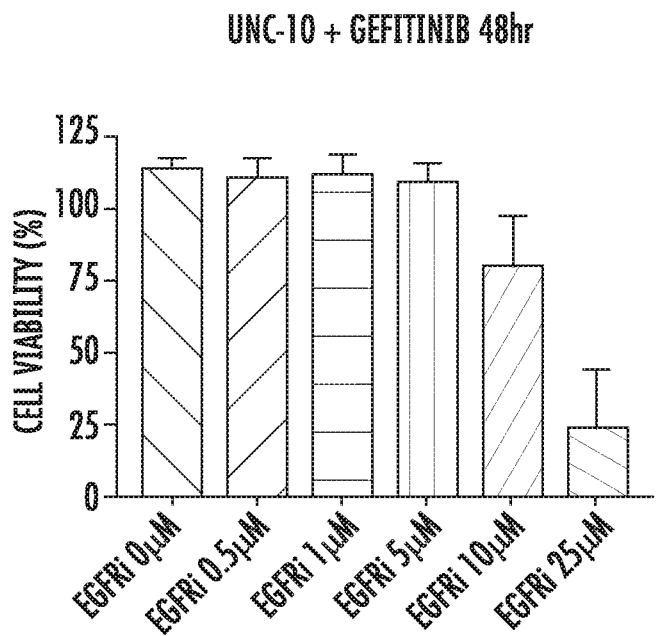
Figure 8C:
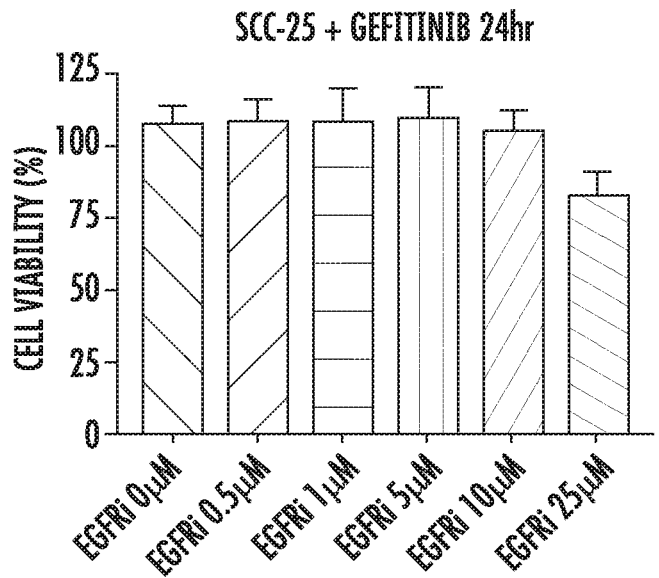
Figure 8D:
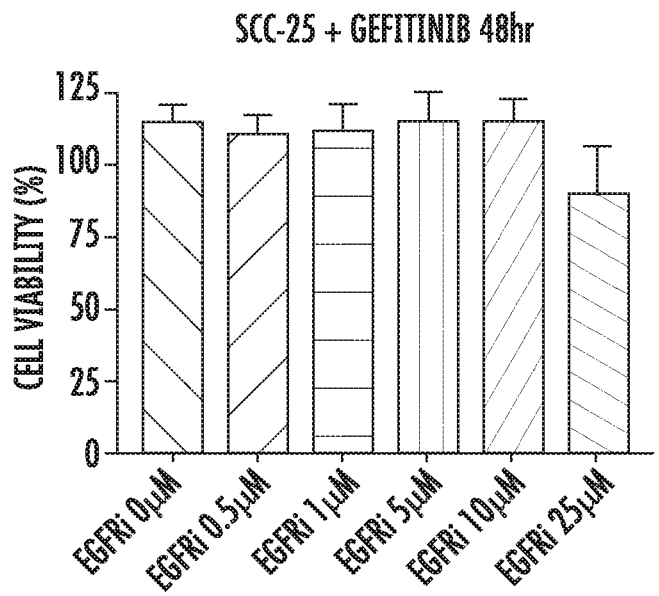
Figure 9A:
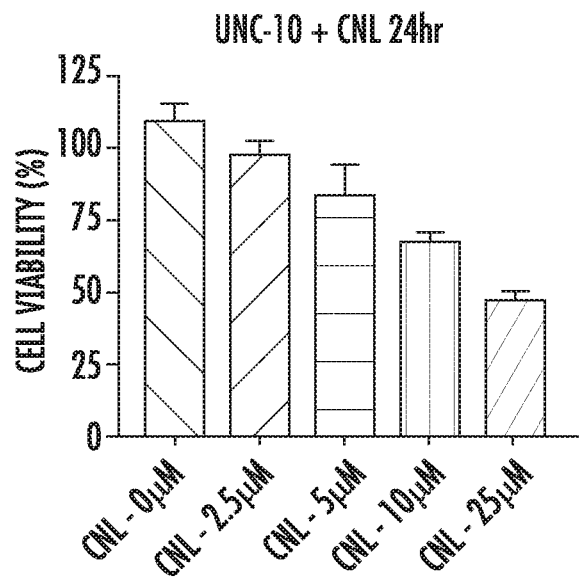
FIGS. 9A-9D are a series of bar graphs showing the results of cell viability as measured by MTS assays of HNSCC cells exposed to various concentrations of CNL for 24 or 48 hours.
Figure 9B:
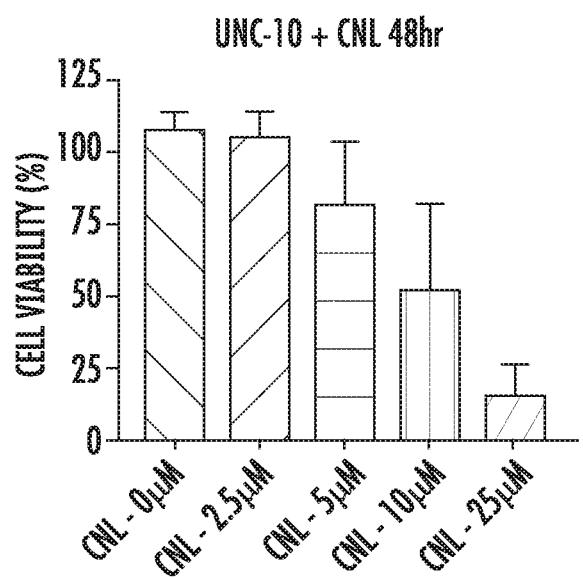
Figure 9C:
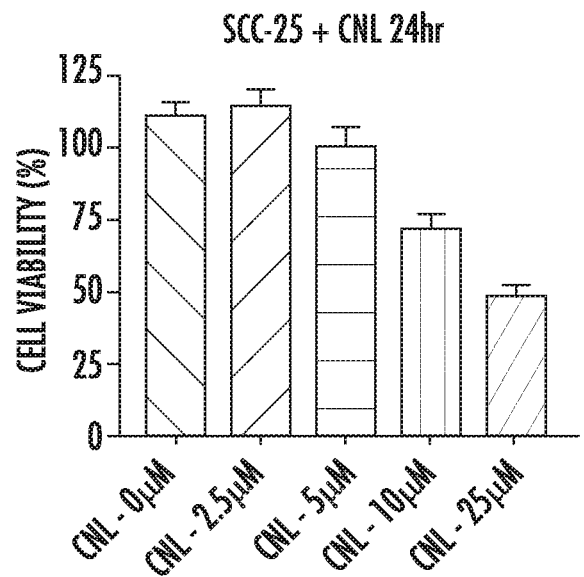
Figure 9D:
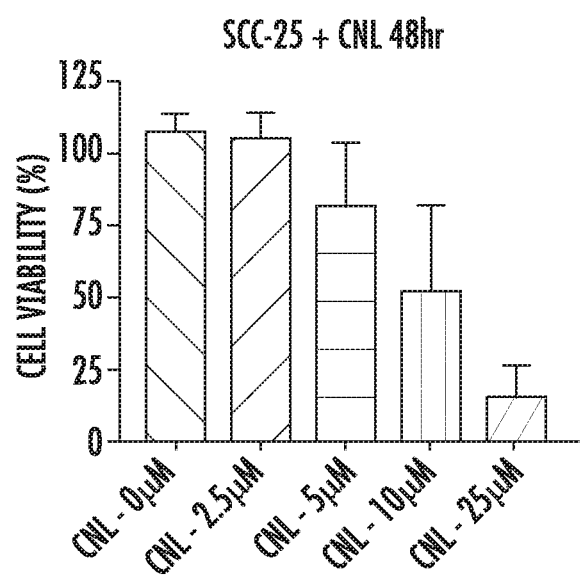

A similar experiment to that described in EXAMPLE 5 was performed to evaluate cell viability in HNSCC cell lines after exposure to Gefitinib. Six different concentrations of Gefitinib were employed: 0 μM, 0.5 μM, 1 μM, 5 μM, 10 μM, & 25 μM. Gefitinib at 5 μM or less had little effect on viability of UNC-10 cells at 24 hours or at 48 hours (FIGS. 8A and 8B, respectively), although higher concentrations reduced viability particularly at 24 hours. The effect was less striking with the SCC-25 cell line at both 24 hours (FIG. 8C) and 48 hours (FIG. 8D).

Example 7

CNL Alone was an Effective Killer of HNSCC Cells

To evaluate cell viability in HNSCC cell lines after exposure to CNLs, similar experiments were performed with five different concentrations of CNLs alone: 0 μM, 2.5 μM, 5 μM, 10 μM, 25 μM. 5,000 UNC-10 or SCC-25 cells were plated in 96-well plates. After 16-30 hours, cells were exposed to each drug alone or in combination, and viability was measured every 24 hours for a total of 48 hours. Viability was assayed using MTS assay (Promega CELL-TITER 96® AQueous Non-Radioactive Cell Proliferation Assay) according to manufacturer instructions. A minimum of three biologically independent experiments were performed. Results were normalized to the respective negative controls of each experiment and are presented in FIGS. 9A-9D.

In both the UNC-10 cells (FIGS. 9A and 9B) and SCC-25 cells (FIGS. 9C and 9D), CNLs showed both a concentration dependent and time dependent reduction in cell viability.

Example 8

CNL Plus EGFR Inhibitor Showed Synergy Against HNSCC Cells

To evaluate cell viability in HNSCC cell lines after exposure to CNLs plus an EGFR inhibitor, 5,000 cells were plated in 96-well plates. After 16-30 hours, cells were exposed to six different concentrations of Erlotinib (0 μM, 0.5 μM, 1 μM, 5 μM, 10 μM, & 25 μM) combined with five different concentrations of CNLs (0 μM, 2.5 μM, 5 μM, 10 μM, & 25 μM), and viability was measured at 24 hours and 48 hours. Viability was assayed using MTS assay (Promega CELLTITER 96® AQueous Non-Radioactive Cell Proliferation Assay) according to manufacturer instructions. A minimum of three biologically independent experiments were performed. Results were normalized to the respective negative controls of each experiment. The results are presented in FIGS. 10A-10D.

Figure 10A:
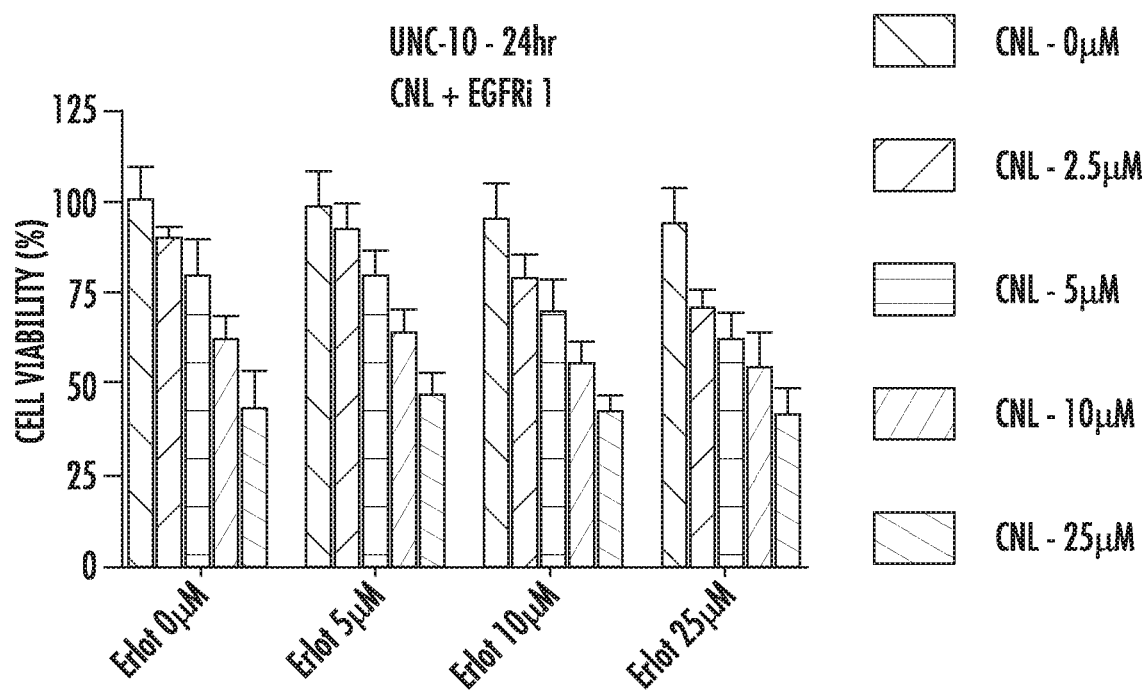
FIGS. 10A-10D are a series of bar graphs showing cell viability as measured by MTS assays of HNSCC cells exposed to various concentrations of CNL and/or the EGFRi Erlotinib (EGFRi 1; Erlot) for 24 or 48 hours.
Figure 10B:
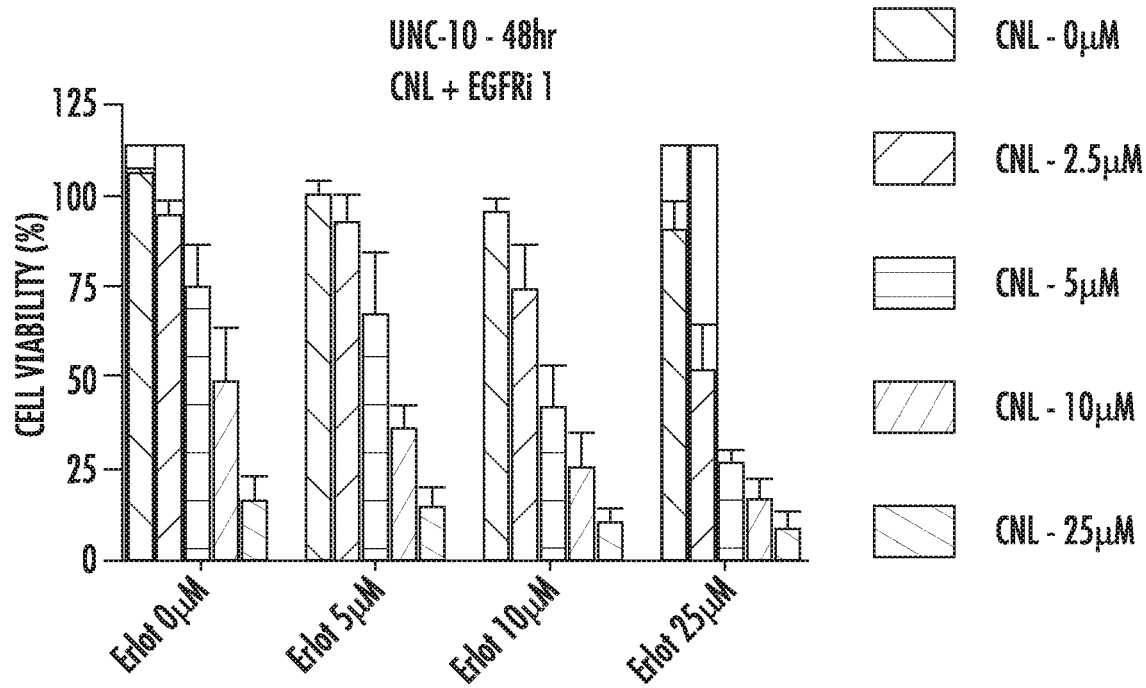
Figure 10C:
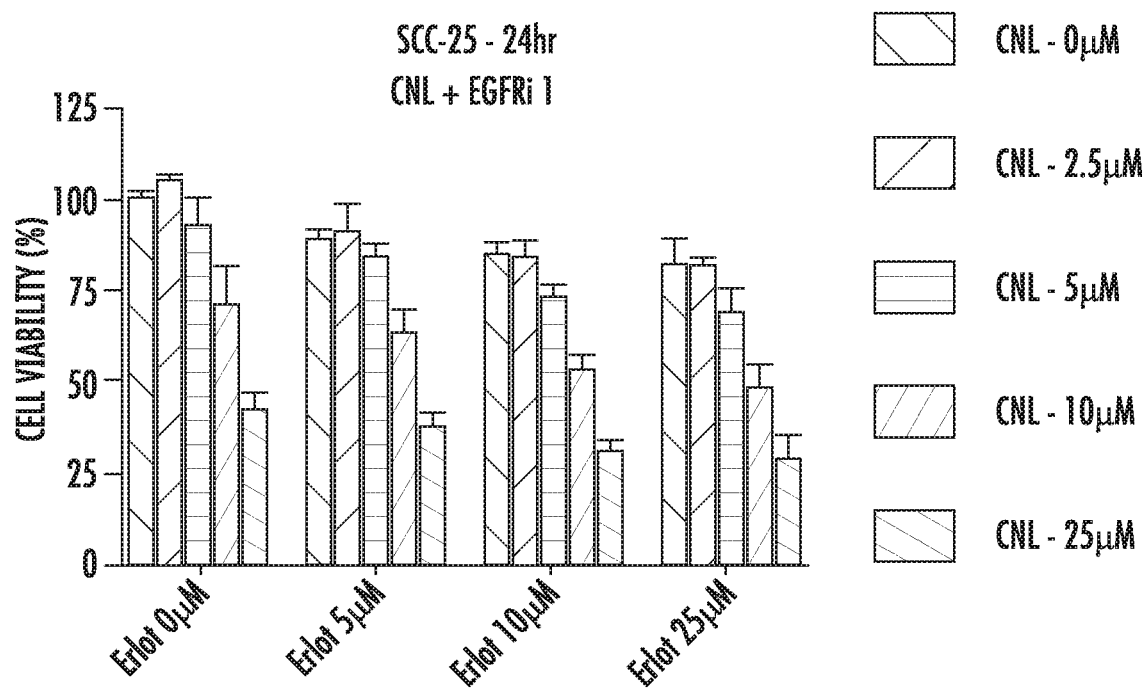
Figure 10D:
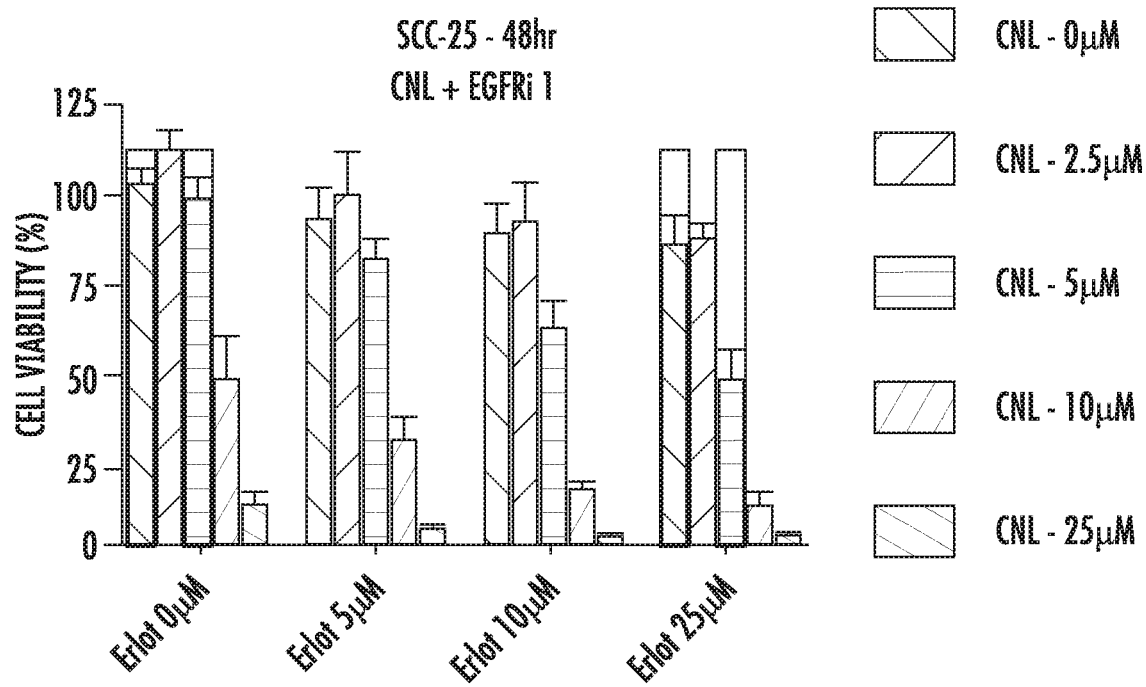

Comparing FIGS. 10A and 10B, control (0 μM Erlotinib and 0 μM CNL) viability was 100% at 24 and 48 hours for UNC-10 cells. At 48 hours, the 2.5 μM CNL alone viability was 95%, and the 25 μM Erlotinib viability was 90%. If the effects of CNL and Erlotinib were merely additive, the 2.5 μM CNL plus 25 μM Erlotinib viability should have been about 85%. Instead, at 48 hours viability in the cells treated with 2.5 μM CNL plus 25 μM Erlotinib was 54%. Thus, 2.5 μM CNL plus 25 μM Erlotinib showed a synergistic effect on UNC-10 cells at 48 hours.

Turning now to the SCC-25 cells (see FIGS. 10C and 10D), control (0 μM Erlotinib and 0 μM CNL) viability was 100% at 24 and 48 hours for these cells. At 48 hours, the 5 CNL alone viability was 98%, and the 25 μM Erlotinib viability was 89%. If the effects of CNL and Erlotinib were merely additive, the 5 μM CNL plus 25 μM Erlotinib viability should have been about 87%. Instead, at 48 hours viability in the cells treated with 5 μM CNL plus 25 μM Erlotinib was 50%. Thus, 5 μM CNL plus 25 μM Erlotinib also showed a synergistic effect on SCC-25 cells at 48 hours.

Similar experiments were performed employing Gefitinib as the EGFR inhibitor, and the results are shown in in FIGS. 11A-11D. Six different concentrations of Gefitinib (0 μM, 0.5 μM, 5 μM, 10 μM, & 25 μM) were tested against five different CNL concentrations (0 μM, 2.5 μM, 5 μM, 10 μM, & 25 μM).

Figure 11A:
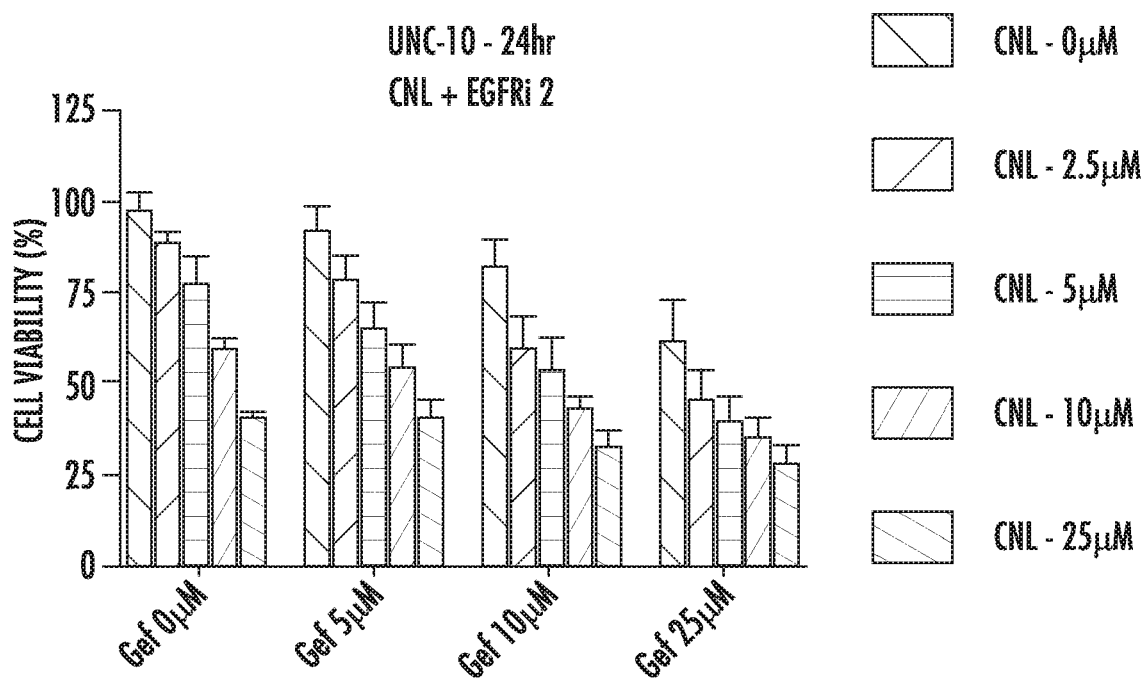
FIGS. 11A-11D are a series of bar graphs showing cell viability as measured by MTS assays of HNSCC cells exposed to various concentrations of CNL and/or the EGFRi Gefitinib (EGFRi 2; Gef) for 24 or 48 hours.
Figure 11B:
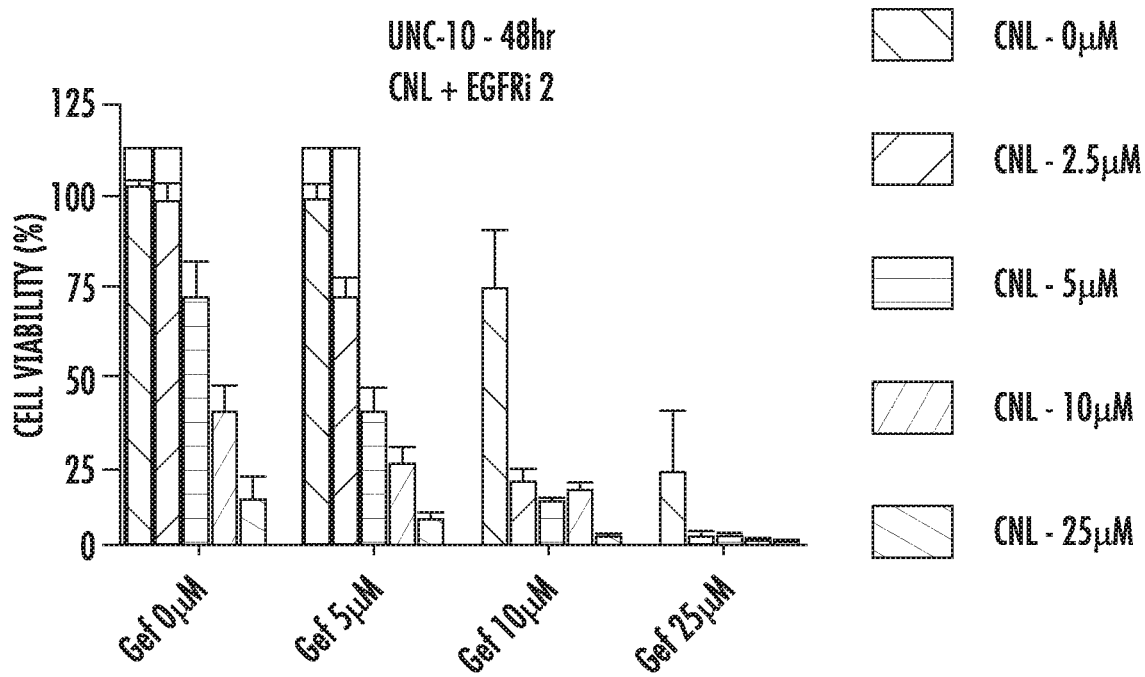
Figure 11C:
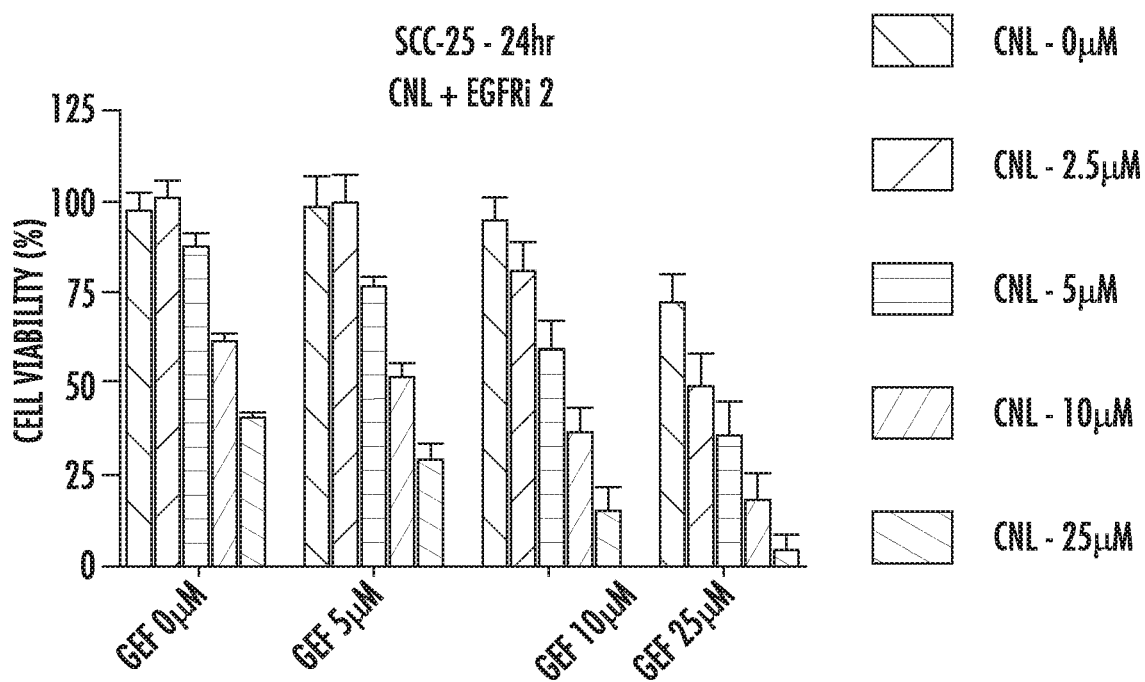
Figure 11D:
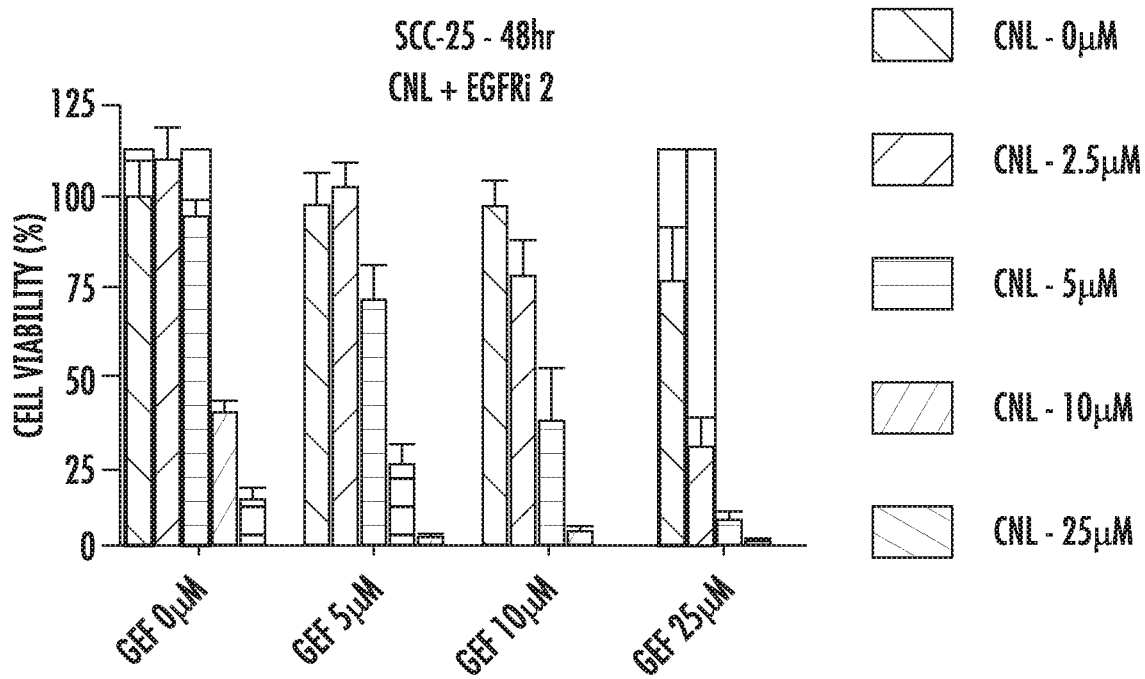

Comparing FIGS. 11A and 11B, control (0 μM Gefitinib and 0 μM CNL) viability was 100% at 24 and 48 hours for UNC-10 cells. At 48 hours, the 2.5 μM CNL alone viability was 96%, and the 5 μM Gefitinib viability was 97%. If the effects of CNL and Gefitinib were merely additive, the 2.5 μM CNL plus 5 μM Gefitinib viability should have been about 93%. Instead, at 48 hours viability in the cells treated with 2.5 μM CNL plus 5 μM Erlotinib was 73%. Thus, 2.5 μM CNL plus 5 μM Erlotinib showed a synergistic effect on UNC-10 cells at 48 hours.

Turning now to the SCC-25 cells (see FIGS. 11C and 11D), control (0 μM Gefitinib and 0 μM CNL) viability was 100% at 24 and 48 hours for these cells. At 48 hours, the 5 μM CNL alone viability was 95%, and the 25 μM Gefitinib viability was 81%. If the effects of CNL and Gefitinib were merely additive, the 5 μM CNL plus 25 μM Gefitinib viability should have been about 76%. Instead, at 48 hours viability in the cells treated with 5 μM CNL plus 25 μM Gefitinib was 9%. Thus, 5 μM CNL plus 25 μM Gefitinib also showed a synergistic effect on SCC-25 cells at 48 hours.

In order to evaluate cell death in HNSCC cell lines exposed to CNL and/or Erlotinib or Gefitinib, flow cytometry assays were also performed. Cells were plated in 24-well plates for 16-30 hours before being pre-treated for one hour with Erlotinib or Gefitinib (0 μM, 10 μM, 25 μM) and then with CNL (0 μM, 2.5 μM, 5 μM). After 24 or 48 hours, cells were stained with a viability dye (Fixable Viability Dye EFLUOR™ 780, ThermoFisher Scientific) according to the manufacturer recommendations. The use of this dye allowed us to differentiate between two cell populations: dead or live cells. Flow cytometry controls (alive/stained, alive/non-stained, & dead/stained) were used to allow for a more rigorous discrimination between populations. Results were normalized to the respective negative controls of each experiment. Data analysis was performed using FlowJo Software. The results are presented in FIGS. 12A-12D.

Figure 12A:
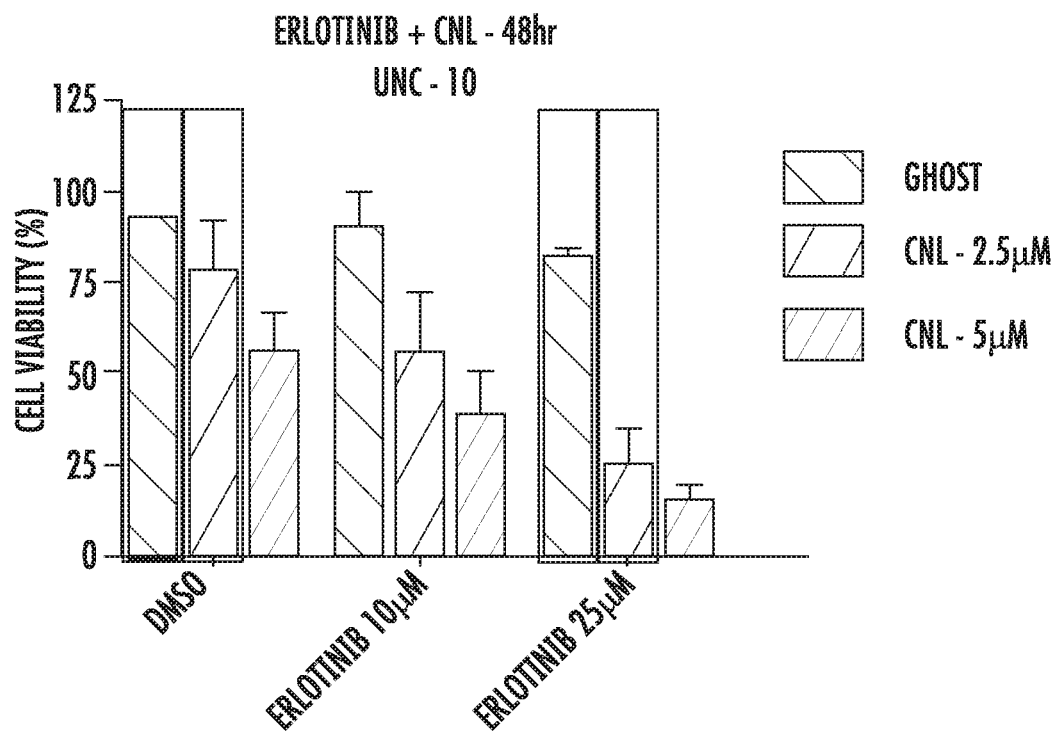
FIGS. 12A-12D are a series of bar graphs showing cell viability assays of HNSCC cells exposed to various concentrations of CNL and/or the EGFRi Erlotinib or the EGFRi Gefitinib for 48 hours.
Figure 12B:
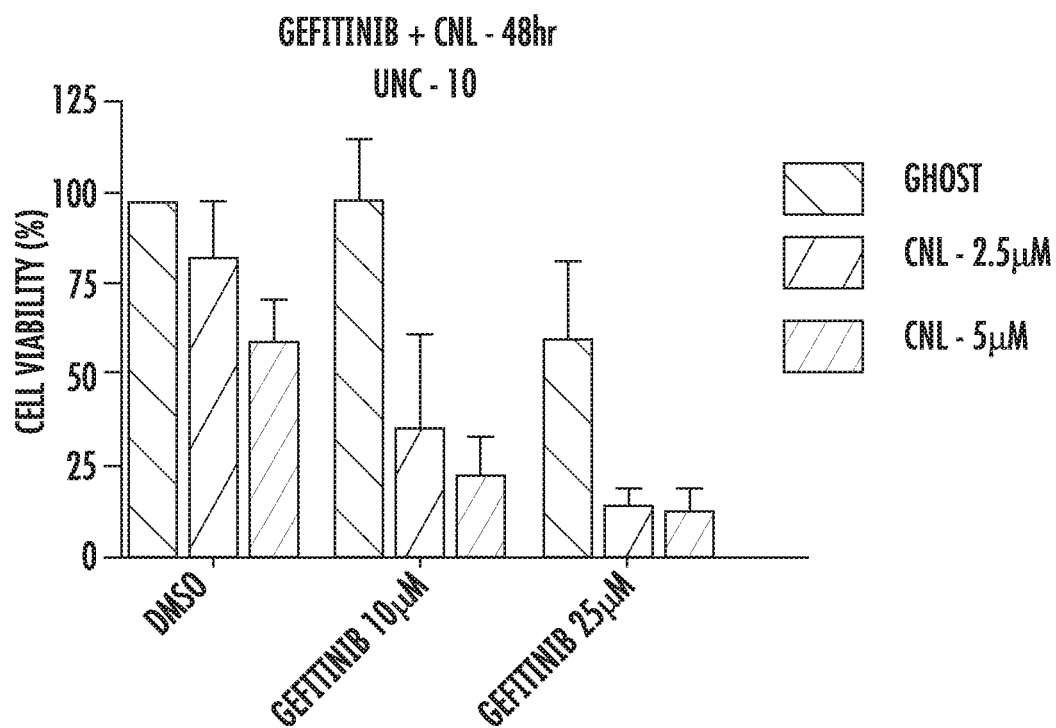

As shown in FIG. 12A, flow cytometry assays determined that control (0 μM Erlotinib and 0 μM CNL) viability was 100% at 48 hours for UNC-10 cells. At 48 hours, the 2.5 μM CNL alone viability was 85%, and the 25 μM Erlotinib viability was 91%. If the effects of CNL and Erlotinib were merely additive, the 2.5 μM CNL plus 25 μM Erlotinib viability should have been about 76%. Instead, at 48 hours viability in the cells treated with 2.5 μM CNL plus 25 μM Erlotinib was 27%. Thus, 2.5 μM CNL plus 25 μM Erlotinib also showed a synergistic effect on UNC-10 cells at 48 hours by flow cytometry. FIG. 12B also demonstrates that Gefitinib plus CNL were more effective at reducing cell viability than Gefitinib or CNL alone.

Figure 12C:
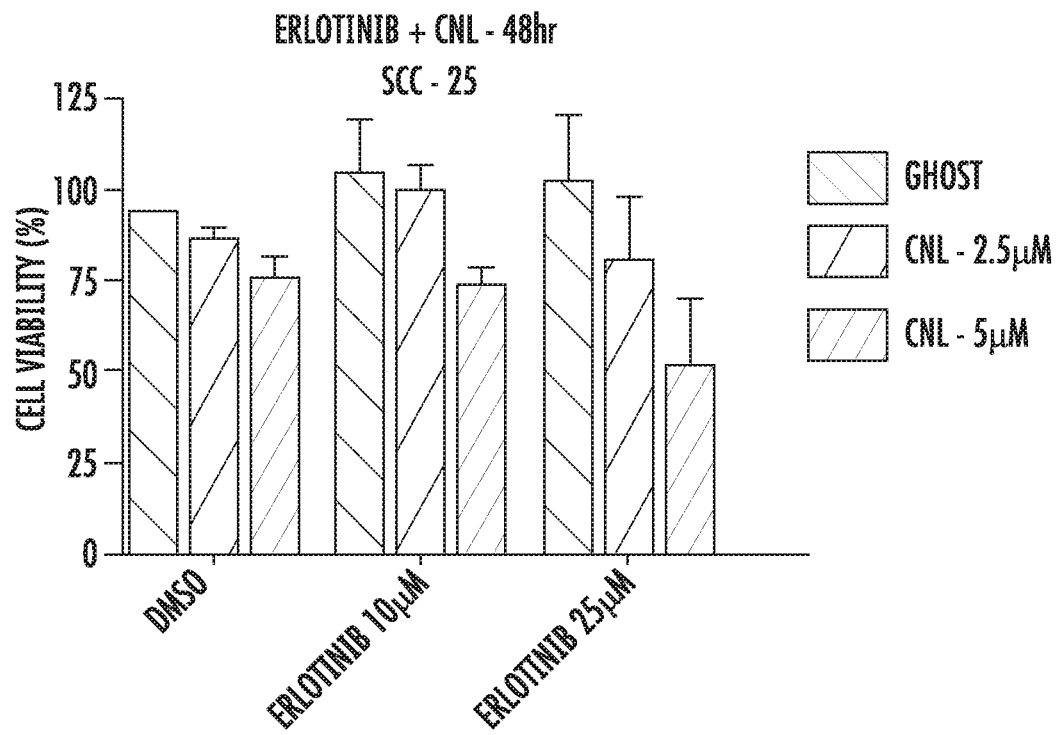
Figure 12D:
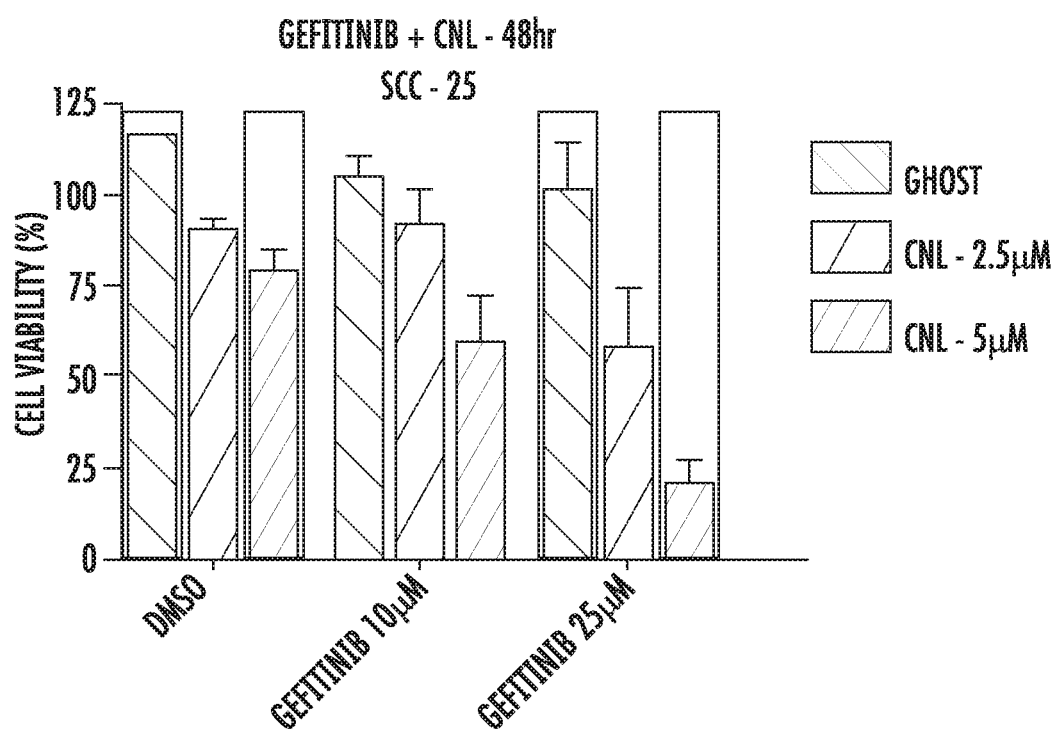
Figure 13A:
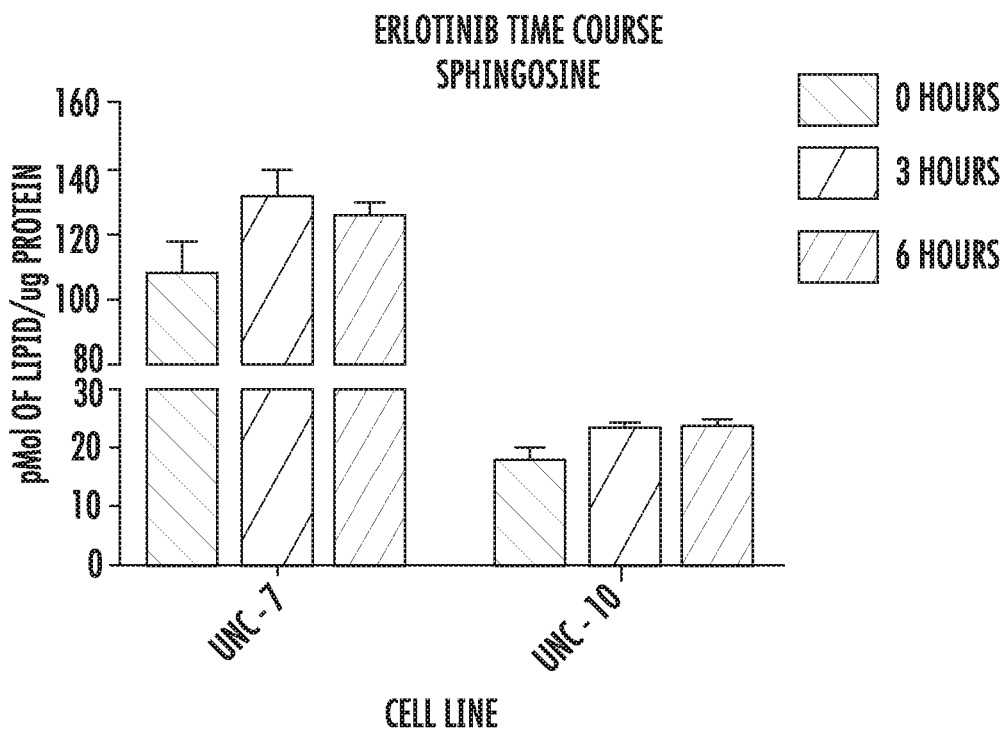
FIGS. 13A-13F are a series of bar graphs depicting the sphingolipid profiles of UNC-7 and UNC-10 HNSCC cells at 0, 3, and 6 hours after exposure to Erlotinib. The bar graphs show picomoles of lipid per microgram of total protein of sphingosine (FIG. 13A), $C_{16}$ ceramide (FIG. 13B), $C_{18}$ ceramide (FIG. 13C), $C_{22:1}$ ceramide (FIG. 13D), $C_{24:1}$ ceramide (FIG. 13E), and $C_{24}$ sphingomyelin (FIG. 13F) for UNC-7 HNSCC cells (left three bars of each Figure) and UNC-10 HNSCC cells (right three bars of each Figure) at 0 hours (left bar of each triad), 3 hours (middle bar of each triad), and 6 hours (right bar of each triad) after exposure to Erlotinib. Each bar represents at least three replicates and error bars represent standard deviation.
Figure 13B:
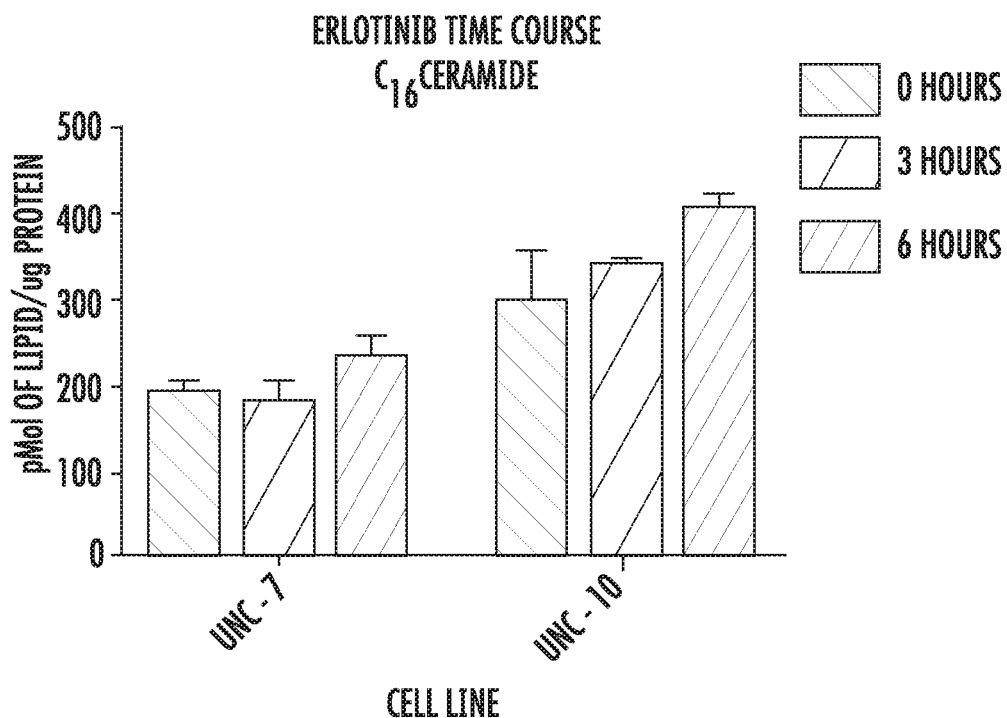
Figure 13C:
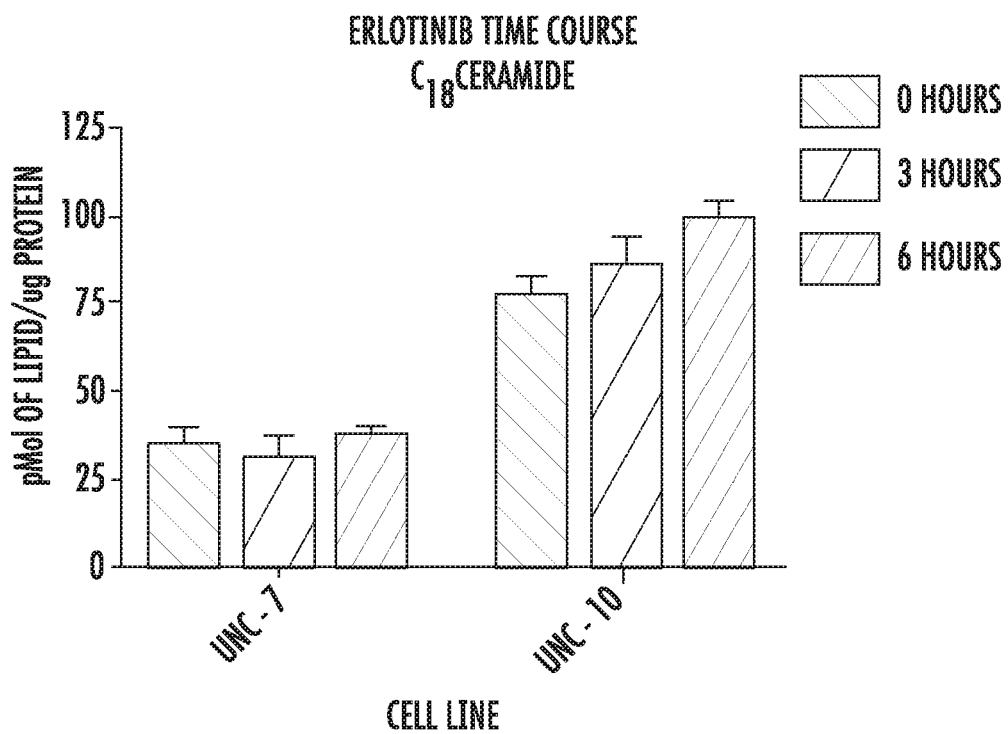
Figure 13D:
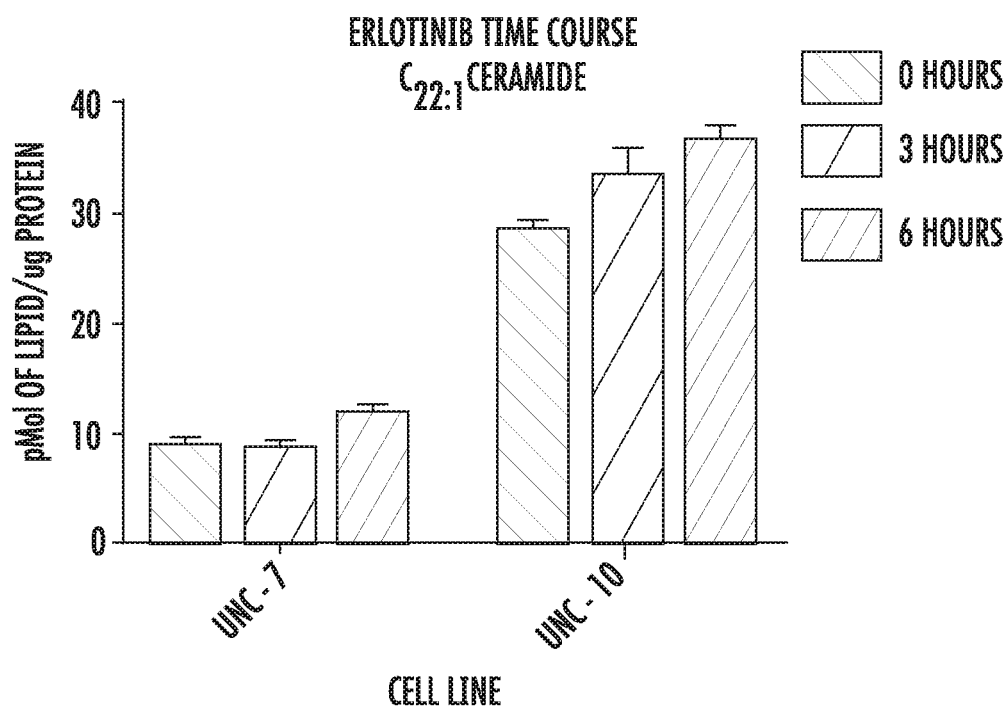
Figure 13E:
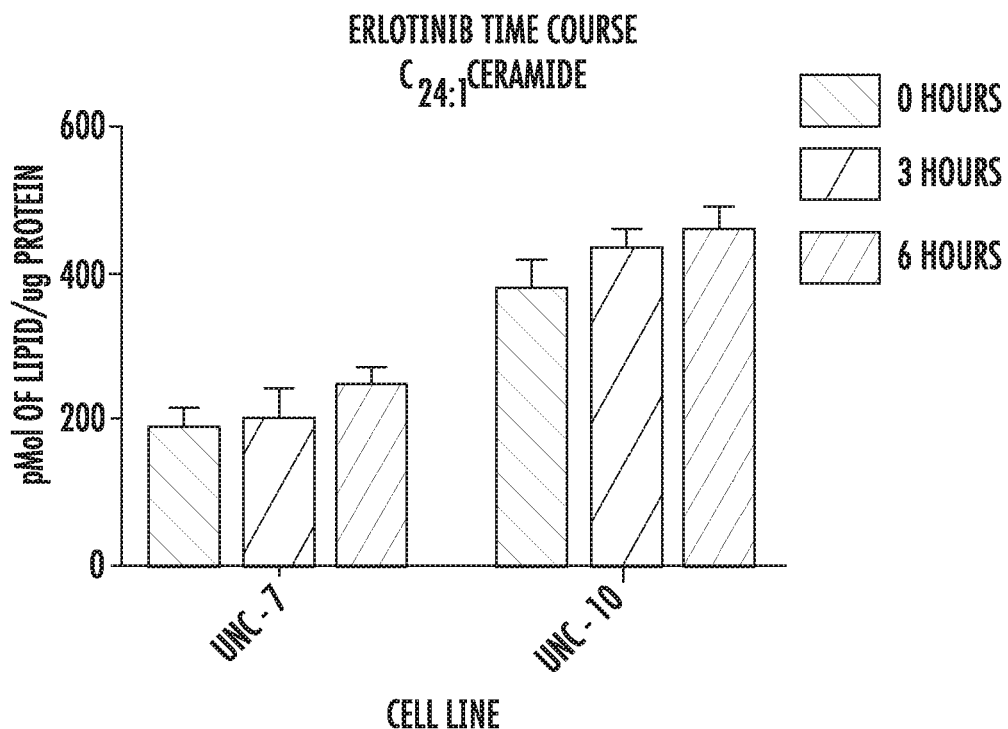
Figure 13F:
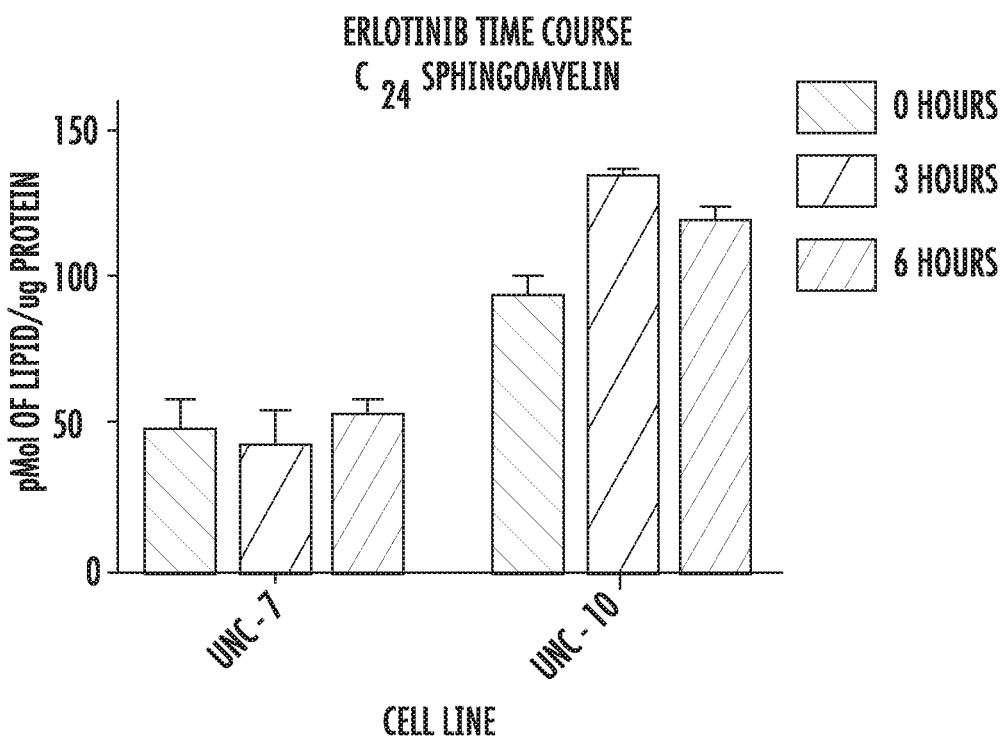

Turning now to FIG. 12C, Erlotinib plus CNL were more effective at reducing viability of SCC-25 cells than Erlotinib or CNL alone. This is also the case for Gefitinib plus CNL as shown in FIG. 12D. At 48 hours, control (0 µM Erlotinib and 0 µM CNL) viability was 100% at 48 hours. At 48 hours, the 5 µM CNL alone viability was 98%, and the 25 µM Erlotinib viability was 89%. If the effects of CNL and Erlotinib were merely additive, the 5 µM CNL plus 25 µM Erlotinib viability should have been about 87%. Instead, at 48 hours viability in the cells treated with 2.5 µM CNL plus 25 µM Erlotinib was 50%. Thus, 5 µM CNL plus 25 µM Erlotinib also showed a synergistic effect on SCC-25 cells at 48 hours by flow cytometry.

Example 9

Erlotinib Altered Levels of Multiple Sphingolipid Species Over Time in HNSCC

To determine Erlotinib's effect on the sphingolipid profile in HNSCC, 500,000 cells of two different cell lines (UNC-7 & UNC-10) were plated and grown in cell culture. When these cells reached about 70% confluence, they were treated with 25 µM Erlotinib. After addition of the Erlotinib, cells were collected immediately, three hours later, or six hours later. Collected cells were lysed using 0.1× PBS and protein quantification was determined using a Pierce BCA Protein Assay (Thermo Fisher Scientific) according to the manufacturer's instructions. Cell lysates containing 250 µg of protein were then used for lipid extractions. The extraction process consisted of adding an organic solvent extraction buffer consisting of isopropanol, water, and ethyl acetate to the samples followed by heating, sonication, and pelleting steps to extract significantly purified lipids. The sphingolipids were then analyzed using LC-MS/MS.

The results are presented in FIGS. 13A-13F. As shown in FIGS. 13A-13F, Erlotinib was able to alter sphingolipid levels, which is believed to be the first report of this activity of Erlonib. Taking together, the presently disclosed results strongly suggested that the combination of Erlotinib and CNL would most likely lead to greatly altered ceramide and sphingolipid metabolism.

Discussion of the EXAMPLES

CNLs were extremely efficient against AR negative cells compared with AR positive cell lines. As disclosed herein, a wide array of PCa cell lines were treated with CNLs and cell viability in these cells after treatment was assayed by MTS assays. These assays were performed for a total of 96 hours with viability being measured every 24 hours. PCa cells that lacked AR were more susceptible to CNLs than AR positive cells. At 48 hours, the $IC_{50}$ values for the AR negative cells tested were less than half of the $IC_{50}$ values for the AR positive cells. One AR positive cell line (LNCaP) and one AR negative cell line (PC-3) were selected to further validate these results using flow cytometry. Again, cellular death was increased after CNL treatment in the AR negative cells, while AR positive cells were resistant to CNL treatment. AR negative cells in the prostate are generally rare, but they are also extremely aggressive in the context of PCa and lack any current efficacious treatment. The findings disclosed herein suggested the potential of CNLs to eradicate AR negative cells of prostate origin in PCa, giving these patients and option that currently does not exist.

Hindering the AR signaling pathway results in a potential synergistic treatment when combined with CNLs. Considering together the inability of CNLs to kill AR positive cells and the ability of AR as a transcription factor to regulate multiple pathways including metabolism, whether blocking AR combined with CNL treatment would result in a better therapeutic option for PCa patients was tested. Two different FDA-approved inhibitors that target the androgen pathway at two different points were chosen. The first, abiraterone acetate, is a CYP17A1 inhibitor that inhibits androgen synthesis per se. The second, Enzalutamide (also called MDV3100), is an AR antagonist that blocks AR signaling pathways. Two AR positive cell lines were treated with both drugs alone as well as in combination with CNL in various concentrations. It was observed that although abiraterone acetate was effective in reducing the viabilities of PCa cells, combination treatment with CNL resulted in even more pronounced reductions in cell viabilities, with AR positive cells being particularly responsive to the treatments. Enzalutamide, on the other hand, was not as effective as a single treatment, but when combined with CNLs resulted in additively or synergistically greater reductions in viability. These results suggested that combining CNLs with AR blockers, already approved for PCa, is as a promising new therapeutic strategy for treatment of PCa, particularly CRPC.

CNLs alone were very effective against HNSCC. CNLs and CNL combination therapies were also tested for the ability to reduce the viabilities of HNSCC cells. Five different concentrations of CNL alone were tested for efficacy in the same eight different HNSCC cell lines. Cell viability was again measured at both 24- and 48-hours post-treatment using MTS cell viability assays. In all eight cell lines, as the concentration of CNL increased, corresponding decreases in cell viability were observed, demonstrating a concentration-dependent effect of CNL on cell death. When comparing the results between 24- and 48-hours post-treatment, each individual concentration was seen to be more effective with longer exposure times, demonstrating a time-dependent effect of CNL on cell death. These results highlighted CNL as a strong potential therapeutic for HNSCC.

EGFR inhibitors were poor monotherapies, but synergistically killed in the presence of CNLs. Six different concentrations of Erlotinib and Gefitinib alone were tested for efficacy in eight different HNSCC cell lines. Cell viability was measured at both 24- and 48-hours post-treatment using MTS cell viability assays. In seven out of the eight cell lines, Gefitinib alone failed to reduce cell viability by more than 25% at its highest concentration at its longest exposure time. Erlotinib was even less effective, failing to produce any meaningful effects in any of the cell lines at any of the concentrations at any of the time points. These findings appeared to replicate the results seen in the failed Erlotinib and Gefitinib HNSCC clinical trials.

The same five concentrations of CNL were combined with the same six concentrations of both Erlotinib and Gefitinib to give a total of 30 drug combinations for each of the eight cell lines. Cell viability was again measured at both 24- and 48-hours post-treatment using MTS cell viability assays. At the highest concentrations of EGFR inhibitors and the lowest concentrations of CNL, synergistic cell death was observed across all eight cell lines. The addition of low concentrations of CNL worked to enhance the effectiveness of both of the EGFR inhibitors, reducing cell viability by an additional 25% when each drug alone did effectively nothing. These findings were then confirmed by flow cytometry using three of the cell lines and the most effective drug combination concentrations. These results highlighted the therapeutic potential of CNLs and EGFR inhibitors in treating a wide variety of HNSCC.

Clinical Significance. Prostate cancer affects hundreds of thousands of men every year worldwide and is estimated to be the second most expensive cancer (cost of care) in 2020 in the United States. Currently hormonal therapies and surgery remain as the gold standard for this cancer despite numerous negative side effects as well as a predicted recurrence rate of the cancer after only 18-24 months in virtually every patient. Nowadays, patients who relapse to these treatments have no other viable option and eventually will die from the disease. Discovery of new compounds that are more effective than current FDA-approved treatments or that improve the efficacy of these previously approved drugs is critical.

The studies disclosed herein suggested that lipid-based therapeutics in the form of a $C_6$-ceramide nanoliposomes (CNL) were extremely efficient against aggressive, AR negative PCa cells while being minimally toxic to non-malignant prostate cells. The response of PCa cells to the combination of CNL and FDA-approved drugs currently being used in the clinic against AR positive PCa indicated that by combining these mildly efficacious drugs with CNL in AR positive PCa cells, these compounds synergized and led to reduced cell viability by increased cell death. In essence, CNL was not only effective alone against AR negative PCa, but synergized with and significantly increased the effects of the current AR inhibitor therapeutics, for AR positive PCa.

The results described herein with respect to PCa were extended to HNSCC. As the seventh most common cancer worldwide, HNSCC effects nearly 700,000 patients a year including nearly 65,000 in the United States alone. Current conventional treatments are costly, painful, can leave patients permanently disfigured, and leave much room for improvement as evidenced by the current 61% 5-year survival rate. In addition to the terrible burden on patients who suffer from this disease, it is also a financial burden in that treatment of HNSCC is set to cost $4.34 billion in the United States alone by 2020. Unfortunately, despite the large volume of cases and poor outcomes for patients, only one targeted therapy exists for HNSCC: cetuximab. However, this targeted therapy has only modest impact. In addition to populations of patients who are allergic to Cetuximab and thus cannot take it, for those who can, the average survival benefit is only around 2-3 months over conventional therapies alone.

Although deemed safe for usage in patients, two other drugs with the same target as Cetuximab—Erlotinib and Gefitinib—failed phase III clinical trials in HNSCC by providing an insignificant therapeutic effect. This was replicated in the in vitro experiments described herein. However, utilizing the presently disclosed CNL alongside Erlotinib or Gefitinib, a new, synergistic, concentration-dependent decrease in cell viability has been demonstrated. In essence, although Erlotinib and Gefitinib failed to provide a significant benefit when used alone, when employed with CNL the combinations proved to be very potent. Perhaps even more striking is that synergy was observed in seven out of eight HNSCC cell lines, suggesting a wide-spread therapeutic benefit for a very heterogenous cancer which has remained elusive to the development of new treatments.

Disclosed herein is the observation that CNLs act more specifically towards cancerous cells than normal cells in the same tissues. The fact that within prostate cancer it was possible to uncover two different responses based on different genetic backgrounds is also believed to be relevant. This is believed to be the first report that distinguished cellular subsets of the same origin based on their hormonal status. Other tumors for which the main drivers are hormones, such as ovarian cancer and breast cancer, could also benefit from the same approach of combining CNLs with hormonal deprivation therapies. Strikingly, AR negative cells have been shown to be relatively unsusceptible to chemotherapeutic agents in vitro and in patients, and so identifying a better treatment strategy for these cells such as is disclosed herein represents a significant clinical advance.

Although not wishing to be bound by any particular theory of operation, a possible mechanism for the synergy between androgen synthesis blockers or AR antagonists with CNLs disclosed herein could be based on the transcription factor role played by AR. AR is a well-known transcription factor that regulates several pathways in cells and is the main driver for normal prostate development, as well as of prostate cancer development and progression. It is possible that AR is able to regulate sphingolipid metabolism by altering sphingolipid metabolic enzymes expression and increase the metabolism of CNLs in prostate cells. When AR is blocked, directly or indirectly, the ability to metabolize these CNLs could be impaired and the accumulation of lipid could lead to cellular death. The combinatorial treatment disclosed herein could then mimic the phenomena observed in AR negative cells. These cells when treated with CNLs were not able to process this lipid leading to cell death.

Furthermore, the use of ceramide-based therapeutics as anti-cancer agents can be unpredictable due to the metabolism of ceramide into more proliferative and tumorigenic lipids such as Sphingosine-1-Phosphate (SIP). Several reports have stated that in vitro and in patients, the levels of S1P were correlated with poor survival and aggressive phenotype (Sekine, 2011; Brizuela, 2014). In fact, some chemotherapeutics have been shown to increase the levels of survival lipids such as S1P after long-term exposure (Krishnamurthy, 2008). By adding an exogenous lipid source that can be converted to pro-survival lipids combined with treatments against PCa that are well-known to promote tumor resistance in the long term, one would not predict that CNLs would be an effective treatment (Han, 2018; Pal, 2018).

Additionally, it has been shown that AR plays dual roles in different cellular pathways, including cell death (Wen, 2014). Therefore, it was unexpected that blocking AR would synergize with a ceramide-based therapeutic. Moreover, the data presented herein suggested that AR antagonism did not change sphingolipid metabolism. However, when combined with CNL treatment, the lipid profile was significantly altered and the ability of the cells to metabolize these exogenous lipids was hindered. There is believed to be no previous disclosure in the literature regarding AR antagonists or androgen synthesis blockers having different mechanisms of action than that displayed when administered as a single treatment. The results disclosed herein suggest a new realm of possibilities for drugs that interfere with the hormonal axis combined with ceramide-based drugs given the different effect these drugs have in the presence of CNLs.

Together, the results presented herein are of extreme clinical relevance since lipid-based therapeutics are starting to hit the clinic, and the therapies disclosed herein showed promise for PCa and HNSCC patients that are currently without any other viable treatment options for their primary diseases, after recurrence, and with respect to metastases therefrom.

Conclusions

It is believed that the present disclosure provided the first showing of the potential of ceramide-based therapeutics for PCa as a single agent or combined with FDA-approved drugs for PCa and HNSCC. As set forth herein, PCa and HNSCC remain difficult and expensive cancers to treat given the recurrence rates for PCa patients treated with AR-targeting therapeutics and HNSCC's heterogeneous nature and limited targeted therapeutic options for patients. Moreover, a small population of cells within the prostate and PCa metastases that are AR negative and extremely aggressive have no current treatment options. Thus, giving how efficacious CNLs are against both AR positive and AR negative PCa cells as well as HNSCC cells, CNLs represent a very promising therapeutic option not just for patients with these cancers but also for patients with metastatic diseases derived therefrom.

REFERENCES

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

Auzenne et al. (1998) 8 Melanoma Res 227-239.
Bose et al. (1995) 82 Cell 405-414.
Brizuela et al. (2014) 8 Molecular Oncology 1181-1195.
Brockerhoff & Ramsammy (1982) 19 Biochim Biophys Acta—Membranes 227-232.
Charles et al. (2001) 47 Cancer Chemother Pharmacol 444-450.
de Villiers et al. (eds) (2009) *Nanotechnology in Drug Delivery*, American Association of Pharmaceutical Scientists Press, Springer, N.Y., New York, United States of America.
Dvir et al. (1991) 113 J Cell Bio 857-865.
Han et al. (2018) 37 Oncogene 710-721.
Krishnamurthy et al. (2008). Deoxycholate promotes survival abreast cancer cells by reducing the level of pro-apoptotic ceramide. 10 Breast Cancer Research R106.
Lu & Oie (2004) *Cellular Drug Delivery: Principles and Practice*, Humana Press Inc., Totowa, New Jersey, United States of America.
Lucci et al. (1999) 86 Cancer 300-311.
Mathias et al. (1998) 335 (Pt. 3) Biochem J 465-480.
Mayer et al. (1986) 40 Chemistry and Physics of Lipids 333-345.
Mehta et al. (2000) 46 Cancer Chemother Pharmacol 85-92.
Myrick et al. (1999) 23 Leuk Res 569-578.
New (1990) *Liposomes: A Practical Approach*, Oxford University Press Inc., New York, New York, United States of America.
Pal et al. (2018) 124 Cancer 1216-1224.
Panek et al. (1997) 283 J Pharm Exp Therap 1433-1444.
Radin (2003) 371 (Pt. 2) Biochem J 243-256.
Reddy et al. (2000) 164 J Immunol 1355-1363.
Sekine et al. (2011) 71 The Prostate 690-699.
Strum et al. (1994) 269 J Biol Chem 15493-15497.
U.S. Pat. Nos. 4,224,179; 5,077,057; 5,558,864; 5,679,683; 6,083,539; 8,747,891; 9,028,863; 9,326,953; 10,045,953.
Wen et al. (2014) 40 Cancer Treatment Reviews 31-40.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for treating Prostate Cancer (PCa) in a subject, the method comprising administering to the subject an effective amount of a ceramide nanoliposome (CNL), wherein the CNL comprises a lipid bilayer comprising one or more $C_2$-$C_{24}$ ceramides and optionally encapsulates an inhibitor of androgen synthesis, an inhibitor of androgen receptor (AR) signaling, or any combination thereof.

2. The method of claim 1, wherein the lipid bilayer of the CNL comprises a $C_6$ ceramide.

3. The method of claim 1, further comprising administering to the subject a second anti-cancer and/or anti-tumor therapy selected from the group consisting of radiotherapy, surgery, an androgen deprivation therapy, and a nuclear receptor inhibitor therapy.

4. The method of claim 3, wherein the second anti-cancer and/or anti-tumor therapy is administered to the subject prior to, concurrently with, or subsequent to administering the effective amount of the CNL to the subject.

5. The method of claim 1, wherein the inhibitor of androgen synthesis and/or androgen receptor (AR) signaling comprises an inhibitor of a CYP17A1 biological activity and/or an AR antagonist.

6. The method of claim 5, wherein the inhibitor of a CYP17A1 biological activity and/or the AR antagonist is selected from the group consisting of abiraterone acetate and enzalutamide.

7. The method of claim 1, wherein the Prostate Cancer (PCa) is associated with the presence of androgen receptor (AR) negative cells in the prostate of the subject.

8. The method of claim 7, wherein the effective amount of the ceramide nanoliposome (CNL) is an amount sufficient to induce apoptosis of the AR negative cells in the prostate of the subject.

9. The method of claim 1, wherein the Prostate Cancer (PCa) is AR-negative PCa and the CNL is administered as a monotherapy.

10. The method of claim 1, wherein the inhibitor of androgen synthesis and/or androgen receptor (AR) signaling is selected from the group consisting of abiraterone acetate, enzalutamide, and analogs thereof.

11. The method of claim 1, wherein the inhibitor of androgen synthesis and/or androgen receptor (AR) signaling is an antibody that binds to an AR or is a paratope-containing fragment or derivative thereof.

12. The method of claim 1, wherein the Prostate Cancer (PCa) is AR-positive PCa and the CNL is administered as a combination therapy with one or more inhibitors of androgen synthesis and/or androgen receptor (AR) signaling.

13. The method of claim 12, wherein the inhibitor of androgen synthesis and/or androgen receptor (AR) signaling is selected from the group consisting of abiraterone acetate, enzalutamide, and analogs thereof.

14. The method of claim 12, wherein the inhibitor of androgen synthesis and/or androgen receptor (AR) signaling is an antibody that binds to an AR or is a paratope-containing fragment or derivative thereof.

15. A method for treating an androgen receptor (AR) negative Prostate Cancer (PCa) in a subject, the method comprising administering to the subject an effective amount of a ceramide nanoliposome (CNL), wherein the CNL comprises a lipid bilayer comprising one or more $C_2$-$C_{24}$ ceramides, and further wherein the effective amount of the ceramide nanoliposome (CNL) is an amount sufficient to induce apoptosis of the AR negative cells in the prostate of the subject to thereby treat the AR negative PCa in the subject.

16. The method of claim 15, further comprising administering to the subject a second anti-cancer and/or anti-tumor therapy selected from the group consisting of radiotherapy, surgery, an androgen deprivation therapy, and a nuclear receptor inhibitor therapy.

17. The method of claim 16, wherein the second anti-cancer and/or anti-tumor therapy is administered to the subject prior to, concurrently with, or subsequent to administering the effective amount of the CNL to the subject.

18. The method of claim 15, further comprising administering to the subject an effective amount of an inhibitor of androgen synthesis.

19. The method of claim 18, wherein the inhibitor of androgen synthesis is an inhibitor of a CYP17A1 biological activity.

20. The method of claim 19, wherein the inhibitor of a CYP17A1 biological activity is abiraterone acetate.

* * * * *